United States Patent
St. Pierre et al.

(10) Patent No.: US 12,236,582 B2
(45) Date of Patent: Feb. 25, 2025

(54) BREAST MAPPING AND ABNORMALITY LOCALIZATION

(71) Applicant: HOLOGIC, INC., Marlborough, MA (US)

(72) Inventors: Shawn St. Pierre, Marlborough, MA (US); Susan Harvey, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 670 days.

(21) Appl. No.: 17/279,002

(22) PCT Filed: Sep. 24, 2019

(86) PCT No.: PCT/US2019/052727
§ 371 (c)(1),
(2) Date: Mar. 23, 2021

(87) PCT Pub. No.: WO2020/068851
PCT Pub. Date: Apr. 2, 2020

(65) Prior Publication Data
US 2022/0036545 A1    Feb. 3, 2022

Related U.S. Application Data

(60) Provisional application No. 62/735,556, filed on Sep. 24, 2018.

(51) Int. Cl.
*G06T 7/00* (2017.01)

(52) U.S. Cl.
CPC .. *G06T 7/0012* (2013.01); *G06T 2207/10081* (2013.01); *G06T 2207/10088* (2013.01);
(Continued)

(58) Field of Classification Search
CPC ......... G06T 7/0012; G06T 2207/10081; G06T 2207/10088; G06T 2207/10116;
(Continued)

(56) References Cited

U.S. PATENT DOCUMENTS

| 3,502,878 A | 3/1970 | Stewart |
| 3,863,073 A | 1/1975 | Wagner |

(Continued)

FOREIGN PATENT DOCUMENTS

| AU | 2014339982 | 4/2015 |
| CN | 1802121 A | 7/2006 |

(Continued)

OTHER PUBLICATIONS

International Search Report and Written Opinion of the International Searching Authority for International Patent Application No. PCT/US2019/052727 mailed Dec. 12, 2019, 15 pages.

(Continued)

*Primary Examiner* — Lewis G West
(74) *Attorney, Agent, or Firm* — Merchant & Gould P.C.

(57) ABSTRACT

Systems and methods for locating abnormalities within a breast and generating mappings of structures, such as ducts, within the breast. First imaging data may be acquired for a breast from a first imaging modality and second imaging data for the breast from a second imaging modality. The first imaging data is co-registered with the second imaging data, such that the first imaging data and the second imaging data share a common coordinate space. Based on the second imaging data, a plurality of structures within the breast are mapped to generate a mapping of the plurality of structures. From at least one of the first imaging data or the second imaging data, the abnormality in the breast is located. The mapping of the plurality of structures and the located abnormality in the breast may be concurrently displayed. A statistical analysis of the mapping of the breast structures may also be performed.

12 Claims, 14 Drawing Sheets

(52) U.S. Cl.
CPC ............... *G06T 2207/10116* (2013.01); *G06T 2207/10132* (2013.01); *G06T 2207/20084* (2013.01); *G06T 2207/30068* (2013.01)

(58) Field of Classification Search
CPC . G06T 2207/10132; G06T 2207/20084; G06T 2207/30068; G06T 2207/10048; A61B 6/0414; A61B 6/4441; A61B 6/4417; A61B 6/502; A61B 6/5217; A61B 6/5247; A61B 8/0825; A61B 8/4416; A61B 8/467; A61B 8/5223; A61B 8/5261; A61B 5/0035; A61B 5/055
See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A * | 7/2000 | Cundari ................. G06T 7/0012 600/407 |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |

(56) References Cited

U.S. PATENT DOCUMENTS

| | | |
|---|---|---|
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 * | 7/2009 | Wang ............... A61B 6/563 600/443 |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 * | 9/2018 | Robinson ............ G06T 7/0012 |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 * | 4/2019 | Reicher .............. G16H 15/00 |
| 10,282,840 B2 * | 5/2019 | Moehrle ............. G06T 7/0014 |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 11,589,944 B2 | 2/2023 | DeFreitas |
| 11,663,780 B2 | 5/2023 | Chen |
| 11,701,199 B2 | 7/2023 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 * | 10/2003 | Suzuki ................ G06T 7/0012 382/156 |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |

(56) References Cited

U.S. PATENT DOCUMENTS

| | | |
|---|---|---|
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1* | 7/2006 | Ma .................. A61P 35/04 705/2 |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0014468 A1 | 1/2007 | Gines et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1 | 3/2009 | Dachille et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1 | 3/2010 | Kojima |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166147 A1 | 7/2010 | Abenaim |
| 2010/0166267 A1 | 7/2010 | Zhang |
| 2010/0171764 A1 | 7/2010 | Feng et al. |
| 2010/0189322 A1 | 7/2010 | Sakagawa |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1* | 9/2010 | Chen .................. G06T 7/0012 382/128 |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0123073 A1* | 5/2011 | Gustafson ............ G06F 3/0482 382/128 |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1 | 6/2011 | Bernard et al. |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014501 A1 | 1/2012 | Pelc |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0127297 A1 | 5/2012 | Baxi |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |

(56) References Cited

U.S. PATENT DOCUMENTS

| | | |
|---|---|---|
| 2012/0148151 A1 | 6/2012 | Hamada |
| 2012/0150034 A1 | 6/2012 | DeFreitas et al. |
| 2012/0189092 A1 | 7/2012 | Jerebko |
| 2012/0194425 A1 | 8/2012 | Buelow |
| 2012/0238870 A1 | 9/2012 | Smith et al. |
| 2012/0277625 A1 | 11/2012 | Nakayama |
| 2012/0293511 A1 | 11/2012 | Mertelmeier |
| 2013/0016255 A1 | 1/2013 | Bhatt |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2013/0272494 A1 | 10/2013 | DeFreitas |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0082542 A1 | 3/2014 | Zhang et al. |
| 2014/0200433 A1 | 7/2014 | Choi |
| 2014/0219534 A1 | 8/2014 | Wiemker et al. |
| 2014/0219548 A1 | 8/2014 | Wels |
| 2014/0276061 A1 | 9/2014 | Lee et al. |
| 2014/0327702 A1 | 11/2014 | Kreeger et al. |
| 2014/0328517 A1 | 11/2014 | Gluncic |
| 2015/0004558 A1 | 1/2015 | Inglese |
| 2015/0052471 A1 | 2/2015 | Chen |
| 2015/0061582 A1 | 4/2015 | Smith |
| 2015/0238148 A1 | 8/2015 | Georgescu |
| 2015/0258271 A1 | 9/2015 | Love |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0210774 A1* | 7/2016 | Wiskin .................. A61B 8/5207 |
| 2016/0228034 A1 | 8/2016 | Gluncic |
| 2016/0235380 A1 | 8/2016 | Smith |
| 2016/0350933 A1* | 12/2016 | Schieke .................. G16H 50/30 |
| 2016/0364526 A1* | 12/2016 | Reicher .................. G06T 11/008 |
| 2016/0367210 A1 | 12/2016 | Gkanatsios |
| 2017/0071562 A1 | 3/2017 | Suzuki |
| 2017/0132792 A1 | 5/2017 | Jerebko et al. |
| 2017/0202453 A1 | 7/2017 | Sekiguchi |
| 2017/0262737 A1 | 9/2017 | Rabinovich |
| 2018/0008220 A1 | 1/2018 | Boone et al. |
| 2018/0008236 A1 | 1/2018 | Venkataraman et al. |
| 2018/0047211 A1 | 2/2018 | Chen et al. |
| 2018/0109698 A1* | 4/2018 | Ramsay .................. A61B 5/4312 |
| 2018/0132722 A1* | 5/2018 | Eggers .................. A61B 5/0033 |
| 2018/0137385 A1 | 5/2018 | Ren |
| 2018/0144244 A1 | 5/2018 | Masoud |
| 2018/0256118 A1 | 9/2018 | DeFreitas |
| 2019/0000318 A1* | 1/2019 | Caluser .................. A61B 5/0073 |
| 2019/0015173 A1 | 1/2019 | DeFreitas |
| 2019/0037173 A1 | 1/2019 | Lee et al. |
| 2019/0043456 A1 | 2/2019 | Kreeger |
| 2019/0057778 A1 | 2/2019 | Porter et al. |
| 2019/0287241 A1* | 9/2019 | Hill .................. A61B 6/5282 |
| 2019/0290221 A1 | 9/2019 | Smith |
| 2019/0325573 A1 | 10/2019 | Bernard et al. |
| 2020/0046303 A1 | 2/2020 | DeFreitas |
| 2020/0054300 A1 | 2/2020 | Kreeger et al. |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2021/0174504 A1 | 6/2021 | Madabhushi |
| 2021/0212665 A1 | 7/2021 | Tsymbalenko |
| 2022/0005277 A1 | 1/2022 | Chen |
| 2022/0013089 A1 | 1/2022 | Kreeger |
| 2022/0192615 A1 | 6/2022 | Chui |
| 2022/0254023 A1 | 8/2022 | McKinney et al. |
| 2022/0386969 A1 | 12/2022 | Smith |
| 2023/0000467 A1 | 1/2023 | Shi |
| 2023/0008465 A1 | 1/2023 | Smith |
| 2023/0033601 A1 | 2/2023 | Chui |
| 2023/0038498 A1 | 2/2023 | Xu |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0098305 A1 | 3/2023 | St. Pierre |
| 2023/0103969 A1 | 4/2023 | St. Pierre |
| 2023/0124481 A1 | 4/2023 | St. Pierre |
| 2023/0125385 A1 | 4/2023 | Solis |
| 2023/0225821 A1 | 7/2023 | DeFreitas |
| 2023/0230679 A1 | 7/2023 | Chen |
| 2023/0240785 A1 | 8/2023 | DeFreitas |
| 2023/0344453 A1* | 10/2023 | Yang .................. H04B 1/04 |
| 2023/0394769 A1 | 12/2023 | Chen |
| 2024/0169958 A1 | 5/2024 | Kreeger |
| 2024/0315654 A1 | 9/2024 | Chui |
| 2024/0320827 A1 | 9/2024 | Chui |

FOREIGN PATENT DOCUMENTS

| | | |
|---|---|---|
| CN | 1846622 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 105193447 | 12/2015 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 A1 | 7/2015 |
| EP | 3060132 | 4/2019 |
| JP | H09-35043 | 2/1997 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |

(56) References Cited

FOREIGN PATENT DOCUMENTS

| | | |
|---|---|---|
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008518684 | 6/2008 |
| JP | 2008-253401 | 10/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005112767 | 6/2005 |
| WO | 2005110230 | 11/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Love, Susan M., et al. "Anatomy of the nipple and breast ducts revisited", Cancer, American Cancer Society, Philadelphia, PA, vol. 101, No. 9, Sep. 20, 2004, pp. 1947-1957.

Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.

European Extended Search Report in Application 19867977.1, mailed Sep. 29, 2022, 18 pages.

European partial Search Report in Application 19867977.1, mailed May 13, 2022, 14 pages.

PCT International Preliminary Report on Patentability in Application PCT/US2019/052727, mailed Apr. 1, 2021, 10 pages.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie. com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", Br J Radiol. Apr. 2010;83 (988):344-50.

Chan, Heang-Ping et al., "Computer-aided detection system for breast masses on digital tomosynthesis mammograms: Preliminary Experience", Radiology, Dec. 2005, 1075-1080.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Cho, N. et al., "Distinguishing Benign from Malignant Masses at Breast US: Combined US Elastography and Color Doppler US-Influence on Radiologist Accuracy", Radiology, 262(1): 80-90 (Jan. 2012).

Conner, Peter, "Breast Response to Menopausal Hormone Therapy—Aspects on Proliferation, apoptosis and Mammographic Density", 2007 Annals of Medicine, 39;1, 28-41.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

(56) References Cited

OTHER PUBLICATIONS

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

Dromain, Clarisse, et al., "Evaluation of tumor angiogenesis of breast carcinoma using contrast-enhanced digital mammography", AJR: 187, Nov. 2006, 16 pages.

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.

E. Shaw de Paredes et al., "Interventional Breast Procedure", published Sep./Oct. 1998 in Curr Probl Diagn Radiol, pp. 138-184.

EFilm Mobile HD by Merge Healthcare, web site: http://itunes.apple.com/bw/app/efilm-mobile-hd/id405261243?mt=8, accessed on Nov. 3, 2011 (2 pages).

EFilm Solutions, eFilm Workstation (tm) 3.4, website: http://estore.merge.com/na/estore/content.aspx?productID=405, accessed on Nov. 3, 2011 (2 pages).

Elbakri, Idris A. et al., "Automatic exposure control for a slot scanning full field digital mammography system", Med. Phys. 2005; Sep; 32(9):2763-2770, Abstract only.

Ertas, M. et al., "2D versus 3D total variation minimization in digital breast tomosynthesis", 2015 IEEE International Conference on Imaging Systems and Techniques (IST), Macau, 2015, pp. 1-4.

Feng, Steve Si Jia, et al., "Clinical digital breast tomosynthesis system: Dosimetric Characterization", Radiology, Apr. 2012, 263(1); pp. 35-42.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Glick, Stephen J., "Breast CT", Annual Rev. Biomed. Eng., 2007, 9;501-26.

Green, C. et al., "Deformable mapping using biochemical models to relate corresponding lesions in digital breast tomosynthesis and automated breast ultrasound images", Medical Image Analysis, 60: 1-18 (Nov. 2019).

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Ijaz, Umer Zeeshan, et al., "Mammography phantom studies using 3D electrical impedance tomography with numerical forward solver", Frontiers in the Convergence of Bioscience and Information Technologies 2007, 379-383.

Jochelson, M., et al, "Bilateral Dual Energy contrast-enhanced digital mammography: Initial Experience", RSNA 2010, 96th Scientific Assembly and Scientific Meeting, 1 page.

Jong, RA, et al., Contrast-enhanced digital mammography: initial clinical experience. Radiology 2003; 228:842-850.

Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.

Kopans, Daniel B., "Breast Imaging", 3rd Edition, Lippincott Williams and Wilkins, published Nov. 2, 2006, pp. 960-967.

Kopans, et. al. Will tomosynthesis replace conventional mammography? Plenary Session SFN08: RSNA 2005.

Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).

Lehman, CD, et al. MRI evaluation of the contralateral breast in women with recently diagnosed breast cancer. N Engl J Med 2007; 356:1295-1303.

Lewin,JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Mahesh, Mahadevappa, "AAPM/RSNA Physics Tutorial for Residents—Digital Mammography: An Overview", Nov.-Dec. 2004, vol. 24, No. 6, 1747-1760.

Metheany, Kathrine G. et al., "Characterizing anatomical variability in breast CT images", Oct. 2008, Med. Phys. 35 (10); 4685-4694.

Niklason, L., et al., Digital tomosynthesis in breast imaging. Radiology. Nov. 1997; 205(2):399-406.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).

Pediconi, "Color-coded automated signal intensity-curve for detection and characterization of breast lesions: Preliminary evaluation of new software for MR-based breast imaging," International Congress Series 1281 (2005) 1081-1086.

Poplack, SP, et al., Digital breast tomosynthesis: initial experience in 98 women with abnormal digital screening mammography. AJR Am J Roentgenology Sep. 2007 189(3):616-23.

Prionas, ND, et al., Contrast-enhanced dedicated breast CT: initial clinical experience. Radiology. Sep. 2010 256(3):714-723.

Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.

Reynolds, April, "Stereotactic Breast Biopsy: A Review", Radiologic Technology, vol. 80, No. 5, Jun. 1, 2009, pp. 447M-464M, XP055790574.

Sakic et al., "Mammogram synthesis using a 3D simulation. I. breast tissue model and image acquisition simulation" Medical Physics. 29, pp. 2131-2139 (2002).

(56) References Cited

OTHER PUBLICATIONS

Samani, A. et al., "Biomechanical 3-D Finite Element Modeling of the Human Breast Using MRI Data", 2001, IEEE Transactions on Medical Imaging, vol. 20, No. 4, pp. 271-279.
Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.
Sechopoulos, et al., "Glandular radiation dose in tomosynthesis of the breast using tungsten targets", Journal of Applied Clinical Medical Physics, vol. 8, No. 4, Fall 2008, 161-171.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Taghibakhsh, f. et al., "High dynamic range 2-TFT amplified pixel sensor architecture for digital mammography tomosynthesis", IET Circuits Devices Syst., 2007, 1(10, pp. 87-92.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Varjonen, Mari, "Three-Dimensional Digital Breast Tomosynthesis in the Early Diagnosis and Detection of Breast Cancer", IWDM 2006, LNCS 4046, 152-159.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Wen, Junhai et al., "A study on truncated cone-beam sampling strategies for 3D mammography", 2004, IEEE, 3200-3204.
Williams, Mark B. et al., "Optimization of exposure parameters in full field digital mammography", Medical Physics 35, 2414 (May 20, 2008); doi: 10.1118/1.2912177, pp. 2414-2423.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Zhang, Yiheng et al., "A comparative study of limited-angle cone-beam reconstruction methods for breast tomosynthesis", Med Phys., Oct. 2006, 33(10): 3781-3795.
Zhao, Bo, et al., "Imaging performance of an amorphous selenium digital mammography detector in a breast tomosynthesis system", May 2008, Med. Phys 35(5); 1978-1987.

\* cited by examiner

BREAST MAPPING AND ABNORMALITY LOCALIZATION

CROSS-REFERENCE TO RELATED APPLICATIONS

This application is a National Stage Application of PCT/US2019/052727, filed Sep. 24, 2019, which claims priority to and the benefit of U.S. Provisional Patent Application No. 62/735,556, filed Sep. 24, 2018, the disclosures of which are hereby incorporated by reference herein in their entireties. To the extent appropriate, a claim of priority is made to each of the above disclosed applications.

BACKGROUND

Medical imaging may be used to imaging devices provide non-invasive methods to visualize the internal structure of a patient. Such non-invasive visualization methods can be helpful in treating patients for various ailments. For example, the visualization methods aid in early detection of cancer or tumors in a patient, which may increase survival probability of patients. In some instances, understanding the particular location of structures within the patient may also be useful in determining next steps in a treatment regime.

One medical imaging technique is ultrasound imaging, which is a non-invasive medical imaging technique that uses sound waves, typically produced by piezoelectric transducers, to image a tissue in a patient. The ultrasound probe focuses the sound waves, typically producing an arc-shaped sound wave which travels into the body and is partially reflected from the layers between different tissues in the patient. The reflected sound wave is detected by the transducers and converted into electrical signals that can be processed by the ultrasound scanner to form an ultrasound image of the tissue.

Other medical imaging processes, such as mammography and tomography, rely primarily on x-ray radiation and are particularly useful tools for imaging breasts to screen for, or diagnose, cancer or other lesions with the breasts. Tomosynthesis, generally, produces a plurality of x-ray images, each of discrete layers or slices of the breast, through the entire thickness thereof. In contrast to typical two-dimensional (2D) mammography systems, a tomosynthesis system acquires a series of x-ray projection images, each projection image obtained at a different angular displacement as the x-ray source moves along a path, such as a circular arc, over the breast.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for mapping the ducts of a breast and localization of abnormalities through one or more medical imaging techniques.

In one aspect, the technology relates to a method for locating an abnormality within a breast. The method includes acquiring first imaging data for a breast from a first imaging modality, wherein the first imaging modality is at least one of an x-ray-based imaging modality or a magnetic resonance imaging (MRI) modality, and acquiring second imaging data for the breast from a second imaging modality, wherein the second imaging modality is at least one of an ultrasound imaging modality or a thermal imaging modality. The method further includes co-registering the first imaging data from the first imaging modality with the second imaging data from the second imaging modality, such that the first imaging data from the first imaging modality and the second imaging data from the second imaging modality share a common coordinate space; mapping, based on the second imaging data from the second imaging modality, a plurality of ducts within the breast to generate a mapping of the plurality of ducts; locating, from at least one of the first imaging data or the second imaging data, the abnormality in the breast; and concurrently displaying the mapping of the plurality of ducts and the located abnormality in the breast. In an example, the method further includes determining that the located abnormality is within one of the plurality of ducts based on the mapping of the plurality of ducts. In another example, the abnormality is a calcification. In yet another example, displaying the mapping of the plurality of ducts and the located abnormality in the breast includes displaying the abnormality as an overlay of a portion of the mapping of the plurality of ducts. In still another example, the mapping is a three-dimensional mapping. In still yet another example, the first imaging data is three-dimensional imaging data acquired from one of tomosynthesis, computed tomography, or MRI. In another example, the first imaging data is mammogram data and the second imaging data is ultrasound imaging data.

In another aspect, the technology relates to a method for imaging a breast. The method includes receiving ultrasound data for a breast scanned with an ultrasound probe; executing an image analysis technique to remove at least a portion of non-ductal tissue from the ultrasound data to generate ductal image data; generating, from the ductal image data, a mapping of the ducts of the breast in a three-dimensional volume; analyzing the mapping of the ducts to determine a statistical correlation between the mapping of the ducts and data for an aggregation of ductal structures for other breasts; and based on the determined statistical correlation, generating a risk assessment for the breast. In an example, the method further includes scanning the breast with the ultrasound probe to generate the ultrasound data; tracking the location of the ultrasound probe during scanning of the breast; and providing visual feedback regarding progress of the scanning. In another example, the risk assessment indicates whether additional diagnostic procedures should be performed for the breast. In yet another example, the image analysis technique comprises an artificial-intelligence technique. In still another example, the method further includes receiving x-ray imaging data for the breast; locating an abnormality in the x-ray imaging data for the breast; and displaying the abnormality in the x-ray imaging data concurrently with at least a portion of the mapping of the ducts. In still yet another example, the method further includes displaying the x-ray imaging data; receiving a selection of a region of interest in the x-ray imaging data; and based on receiving the selection of the region of interest, displaying a portion of the mapping of the ducts corresponding to the selected region of interest. In another example, the method further includes determining that the located abnormality is within one of the plurality of ducts based on the mapping of the ducts.

In another aspect, the technology relates to a system for imaging ducts of a breast. The system includes a display; at least one processor operatively connected to the display; and memory, operatively connected to the at least one processor, storing instructions that when executed by the at least one processor cause the system to perform a set of operations. The set of operations includes receiving ultrasound data during a scan of the breast with an ultrasound probe; based on the ultrasound data, generating a three-dimensional mapping of the ducts of the breast; receiving x-ray imaging data for the breast; locating an abnormality in the x-ray imaging data for the breast; and displaying the abnormality in the x-ray imaging data concurrently with at least a portion of the three-dimensional mapping of the ducts. In an example, the operations further include determining that the located abnormality is within one of the ducts of the breast based on the three-dimensional mapping of the ducts. In another example, the operations further include tracking the location of the ultrasound probe during the scan of the breast; and providing visual feedback regarding progress of the scanning during the scan of the breast. In yet another example, the operations further include displaying the x-ray imaging data; receiving a selection of a region of interest in the x-ray imaging data; and based on receiving the selection of the region of interest, displaying a portion of the three-dimensional mapping of the ducts corresponding to the selected region of interest. In still another example, the operations further include analyzing the three-dimensional mapping of the ducts to determine a statistical correlation between the mapping of the ducts and data for an aggregation of ductal structures for other breasts; and based on the determined statistical correlation, generating a risk assessment for the breast. In still yet another example, the risk assessment indicates whether additional diagnostic tests should be performed for the breast.

In another aspect, the technology relates to a method for locating an abnormality within a breast. The method includes acquiring first imaging data for a breast from a first imaging modality, wherein the first imaging modality is at least one of an x-ray-based imaging modality or a magnetic resonance imaging (MRI) modality, and acquiring second imaging data for the breast from a second imaging modality, wherein the second imaging modality is at least one of an ultrasound imaging modality or a thermal imaging modality. The method also includes, based on the second imaging data from the second imaging modality, generating a model of the one or more structures within the breast to generate a mapping of the one or more structures; locating, from at least one of the first imaging data or the second imaging data, the abnormality in the breast; and based at least on the generated model of the one or more structures, determining a location of the abnormality relative to modeled one or more structures within the breast.

In an example, the method further includes displaying at least a portion of a visual representation of the model concurrently with the abnormality. In another example, the one or more structures are breast ducts. In yet another example, the one or more structures are at least one of breast ducts, lobules, lymph nodes, vascular structures, or Cooper's ligaments. In a further example, determining the location of abnormality relative to modeled one or more structures within the breast includes determining whether the abnormality is within one of the one or more structures. In still another example the first imaging data is three-dimensional imaging data acquired from one of tomosynthesis, computed tomography, or MRI. In still yet another example, the first imaging data is mammogram data and the second imaging data is ultrasound imaging data. In another example, the method further comprises: co-registering the first imaging data from the first imaging modality with the second imaging data from the second imaging modality, such that the first imaging data from the first imaging modality and the second imaging data from the second imaging modality share a common coordinate space.

In another aspect, the technology relates to a method for imaging a breast. The method includes receiving ultrasound data for a breast scanned with an ultrasound probe; executing an image analysis technique to identify one or more anatomical structures of the breast; generating, from the identified one or more anatomical structures, a mapping of the one or more structures of the breast; analyzing the mapping of the one or more anatomical structures to determine a statistical correlation between the mapping of the one or more anatomical structures and data for an aggregation of mappings of the one or more anatomical structures for other breasts; and based on the determined statistical correlation, generating a risk assessment for the breast.

In an example, the method further includes scanning the breast with the ultrasound probe to generate the ultrasound data; tracking the location of the ultrasound probe during scanning of the breast; and providing visual feedback regarding progress of the scanning. In another example, the risk assessment indicates whether additional diagnostic procedures should be performed for the breast. In yet another example, the image analysis technique comprises an artificial-intelligence technique. In still another example, the one or more anatomical structures are breast ducts. In still yet another example, the method further includes extracting from the generated mapping, quantitative values at least one of the number of ducts, a regularity pattern for the ducts, or a termination regularity for the ducts; and wherein the statistical correlation is based on the extracted quantitative values.

In another example, the one or more anatomical structures are at least one of breast ducts, lobules, lymph nodes, vascular structures, or Cooper's ligaments. In a further example, the ultrasound data is 3D ultrasound data for the whole breast.

In another aspect, the technology relates to a system for imaging ducts of a breast. The system includes at least one processor; and memory, operatively connected to the at least one processor, storing instructions that when executed by the at least one processor cause the system to perform a set of operations. The set of operations include receiving ultrasound data for a breast scanned with an ultrasound probe; executing an image analysis technique to identify one or more anatomical structures of the breast; generating, from the identified one or more anatomical structures, a mapping of the one or more anatomical structures of the breast; extracting at least one feature from the mapping of the one or more anatomical structures; comparing the extracted at least one feature to a threshold value; and based on the comparison of the extracted at least one feature to the threshold value, generating a risk assessment for the breast.

In an example, the threshold is based on an aggregate of mapping for the one or more anatomical structures. In another example, the one or more anatomical structures are at least one of breast ducts, lobules, lymph nodes, vascular structures, or Cooper's ligaments. In yet another example, the extracted at least one feature is represented by a quantitative value.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIG. 1I depicts an example of the ultrasound imaging system in use with breast of a patient.

DETAILED DESCRIPTION

Figure 1A:
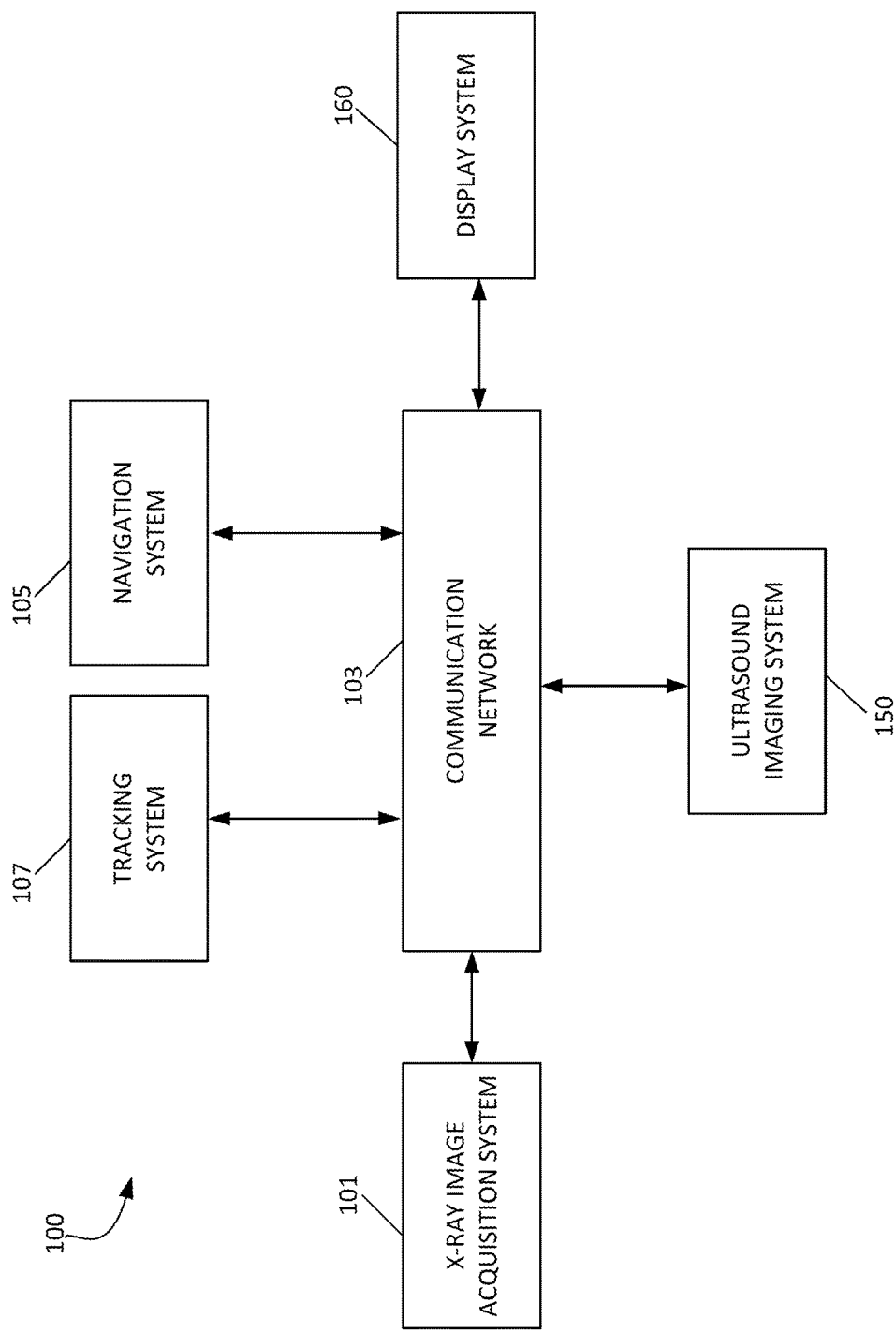
FIG. 1A depicts an example medical imaging system for breast mapping and abnormality localization.

Detection and localization of abnormalities within a breast may be an important part in diagnosing a type of abnormality, or in some examples, a type of cancer. For instance, the location of a lesion or a calcification in relation other structures of the breast may provide additional information that may be useful for diagnostics. The relative location of abnormalities, such as lesions or calcifications, to structures such as breast ducts lobules, Cooper's ligaments, dense tissue, fat, skin, vascular structures, and/or lymph nodes may all provide additional diagnostic information. As an example, whether an abnormality is located in a duct of a breast may be informative as to what type of cancer the abnormality may correspond. In particular, the location of the abnormality relative to the breast ducts in useful in the classification as ductal carcinoma in situ (DCIS). DCIS is a non-invasive cancer where abnormal cells are found in a duct of the breast. If the abnormal cells are confined within the duct, the cancer is generally very treatable by a variety of treatment options. In contrast, if abnormal cells are located outside of the breast ducts, the cancer is likely to be more invasive and spread more quickly. Currently, DCIS is often diagnosed based on a pattern of abnormalities displaying as bright dots within a mammogram. Depending on the shape or pattern of the dots, a prediction is made as to whether the patient has DCIS. There is no determination, however, as to whether the abnormalities are actually confined to a breast duct. As such, it would be beneficial to be able to identify through non-invasive medical imaging whether an abnormality is located inside or outside of a breast duct.

Current medical imaging systems are limited in their ability to provide such an indication or relationship between abnormalities and other breast structures. For example, while x-ray imaging systems are generally effective for identifying some abnormalities (such as calcifications), the identification of other structures (such as breast ducts) through x-ray imaging is difficult. In contrast, ultrasound imaging systems are generally effective at identifying tissue such as ducts, but may not be as effective at identifying abnormalities. X-ray based imaging may also be somewhat limited in dense tissue, whereas ultrasound imaging often performs well in dense tissue. To leverage the benefits of both imaging modalities, the present technology provides for combining x-ray imaging data with ultrasound imaging data to provide an indication or determinations regarding the location of abnormalities in relation to other structures or features of the breast. For instance, the present technology may be used to provide an indication or determination as to whether abnormalities are located inside or outside the ducts of the breast. For example, a tomosynthesis system may be used to image a breast of a patient and an ultrasound system may also be used to image the breast. The imaging data from the tomosynthesis system may be co-registered with the imaging data from the ultrasound imaging system, such that a location in the tomosynthesis imaging data may be correlated with imaging data from the ultrasound imaging system. The structures of the breast may be also be mapped to form a 3D mapping of the structures of the breast. For example, the ducts of the breast may be mapped so as to form a 3D mapping of the ducts in the breast. An abnormality may be located or identified in the x-ray imaging data. The abnormality may then be overlaid, visually or mathematically, on the mapping of the ducts to determine whether the abnormality lies inside or outside one the structures, such as a duct.

In addition, the mapping of the breast structures, such as ducts, may also be used to determine a risk factor for different types of cancers or other conditions. Particular patterns and configurations of structures within a breast may be indicative of a higher risk for invasive cancers, whereas other patterns and configurations of structures may indicate a lower risk for such invasive cancers. Accordingly, the present technology may analyze the 3D mapping of the ducts to determine a statistical correlation between the mapping of structures and data for an aggregation of the same type of structures from other breasts. Based on the determined statistical correlation, a risk assessment for the analyzed breast may be determined. If the risk is considered high, additional procedures may be recommended for the patient to determine if any cancerous cells are present in the breast.

In describing examples and embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIG. 1A depicts an example medical imaging system 100 for breast mapping and abnormality localization. System 100 includes an x-ray image acquisition system 101, a tracking system 107, an ultrasound imaging system 150, a navigation system 105 and a display system 160, all representatively connected via communication network 103. It should be noted that, although the 'systems' are shown in FIG. 1 as functional blocks, different systems may be integrated into a common device, and the communication link may be coupled between fewer than all of the systems; for example, the tracking system 107, navigation system 105 and display system 160 may be included in an acquisition work station or a technologist work station which may control the acquisition of the x-ray images in a radiology suite. Alternatively, the navigation system 107 and tracking system 105 may be integrated into the ultrasound system 150, or provided as standalone modules with separate communication links to the display 160, x-ray acquisition system 101 and ultrasound system 150. Similarly, skilled persons will additionally appreciate that communication network 103 can be a local area network, wide area network, wireless network, internet, intranet, or other similar communication network.

In one embodiment, x-ray image acquisition system 101 is a tomosynthesis acquisition system which captures a set of projection images of a patient's breast as an x-ray tube scans across a path over the breast. The set of projection images is subsequently reconstructed to a three-dimensional volume which may be viewed as slices or slabs along any plane. The three-dimensional volume may be stored locally on x-ray imaging system 101 or in some embodiments in a database or other storage means. Additional details regarding an example x-ray image acquisition system are depicts in FIGS. 1B-1G.

X-ray imaging system 101 may transmit the three-dimensional x-ray image volume to navigation system 105 via communication network 103, where such x-ray image can be stored and viewed. Skilled persons will understand that the x-ray image of a patient can, in alternative embodiments, be stored locally on x-ray imaging system 101 and accessed remotely by navigation system 105 via communications network 130, and in other embodiments can be stored on a server in communication with navigation system 105 via communications network 103. Navigation system 105 displays the x-ray image obtained by x-ray imaging system and once reconstructed for display on navigation system 105 the x-ray image can be reformatted and repositioned to view the image at any plane and any slice position or orientation. In some embodiments navigation system 105 displays multiple frames or windows on the same screen showing alternative positions or orientations of the x-ray-image slice.

Skilled persons will understand that the x-ray image volume obtained by x-ray imaging system 101 can be transmitted to navigation system 105 at any point in time and is not necessarily transmitted immediately after obtaining the x-ray image volume, but instead can be transmitted on the request of navigation system 105. In alternative embodiments, the x-ray image volume is transmitted to navigation system 105 by a transportable media device, such as a flash drive, CD-ROM, diskette, or other such transportable media device.

Ultrasound imaging system 150 obtains an ultrasound image of a tissue of a patient, typically using an ultrasound probe, which is used to image a portion of a tissue of a patient within the field of view of the ultrasound probe. For instance, the ultrasound imaging system 150 may be used to image a breast, and more specifically, structures such as the ducts of a breast. Ultrasound imaging system 150 obtains and displays an ultrasound image of a patient's anatomy within the field of view of the ultrasound probe and typically displays the image in real-time as the patient is being imaged. In some embodiments, the ultrasound image can additionally be stored on a storage medium, such as a hard drive, CD-ROM, flash drive or diskette, for reconstruction or playback at a later time. Additional details regarding the ultrasound imaging system are depicted in FIGS. 1G-1I.

In some embodiments, navigation system 150 can access the ultrasound image, and in such embodiments ultrasound imaging system 150 is further connected to communication network 103 and a copy of the ultrasound image obtained by ultrasound imaging system 150 can be transmitted to navigation system 105 via communication network 103. In other embodiments, navigation system 105 can remotely access and copy the ultrasound image via communication network 103, and in alternative embodiments, a copy of the ultrasound image can be stored on a server in communication with navigation system 105 via communications network 103 and accessed remotely by navigation system 105.

Tracking system 107 is in communication with navigation system 105 via communications network 130 and may track the physical position in which ultrasound imaging system 150 is imaging the tissue of the patient. In some embodiments, tracking system 107 can be connected directly to navigation system 105 via a direct communication link or wireless communication link. Tracking system 107 tracks the position of transmitters connected to ultrasound imaging system 150 and provides navigation system 105 with data representing their coordinates in a tracker coordinate space. In some embodiments, tracking system may be an optical tracking system comprising an optical camera and optical transmitters, however skilled persons will understand that any device or system capable of tracking the position of an object in space can be used. For example, skilled persons will understand that in some embodiments an RF tracking system can be used, comprising an RF receiver and RF transmitters.

Ultrasound imaging system 150 may be configured for use with navigation system 105 by a calibration process using tracking system 107. Transmitters that are connected to the ultrasound probe of ultrasound imaging system 105 may transmit their position to tracking system 107 in the tracker coordinate space, which in turn provides this information to navigation system 105. For example, transmitters may be positioned on the probe of ultrasound imaging system 150 so that tracking system 107 can monitor the position and orientation of the ultrasound probe and provide this information to navigation system 105 in the tracker coordinate space. Navigation system 105 may use this tracked position to determine the position and orientation of the ultrasound probe, relative to the tracked position of the transmitters.

In some examples, configuration occurs using a configuration tool. In such example, the position and orientation of the configuration tool may be additionally tracked by tracking system 107. During configuration the configuration tool contacts the transducer face of the ultrasound probe of ultrasound imaging system 150 and tracking system 107 transmits information representing the position and orientation of the configuration tool in the tracker coordinate space to navigation system 105. Navigation system 105 may determine a configuration matrix that can be used to determine the position and orientation of the field of view of the ultrasound probe in the tracker coordinate space, based on the tracked position of the transmitters connected to the ultrasound probe. In alternative embodiments, a database having configuration data of a plurality of brands or models of various ultrasound probes can be used to pre-load a field of view configuration into navigation system 105 during configuration.

Once ultrasound imaging system 150 is configured with navigation system 105, the tissue of a patient can be imaged with ultrasound imaging system 150. During ultrasound imaging, tracking system 107 monitors the position and orientation of the ultrasound probe of ultrasound imaging system 150 and provides this information in the tracker coordinate space to navigation system 105. Since ultrasound imaging system 150 has been configured for use with navigation system 105, navigation system 105 is able to determine position and orientation of the field of view of the ultrasound probe of ultrasound imaging system 150.

Navigation system 105 can be configured to co-register an ultrasound image with an x-ray image. In some embodiments, navigation system 130 can be configured to transform the position and orientation of the field of view of the ultrasound probe from the tracker coordinate space to a position and orientation in the x-ray image, for example, to x-ray system coordinates. This can be accomplished by tracking the position and orientation of the ultrasound probe and transmitting this positional information in the tracker coordinate space to navigation system 105 and relating this positional information to the x-ray coordinate system. For example, in some embodiments, a user can select an anatomical plane within the x-ray image, and the user can then manipulate the position and orientation of a tracked ultrasound probe to align the field of view of the ultrasound probe with the selected anatomical plane. Once alignment is achieved, the associated tracker space coordinates of the ultrasound image can be captured. Registration of the anatomic axes (superior-inferior (SI), left-right (LR) and anterior-posterior (AP)) between the x-ray image and the tracker coordinate space can be determined from the relative rotational differences between the tracked ultrasound field of view orientation and the selected anatomical plane using techniques known to those of skill in the art.

This configuration may further include the selection of landmark within the x-ray image, for example, using an interface permitting a user to select an anatomical target. In some embodiments, the landmark can be an internal tissue landmark, such as veins or arteries, and in other embodiments, the landmark can be an external landmark, such as a fiducial skin marker or external landmark, such as a nipple. The same landmark selected in the x-ray image can be located with the ultrasound probe, and upon location, a mechanism can be provided for capturing coordinates of the representation of the target in the tracker coordinate space. The relative differences between the coordinates of the target in the x-ray image and the coordinates of the target in the tracker coordinate space are used to determine the translational parameters required to align the two co-ordinate spaces. The plane orientation information acquired previously can be combined with the translation parameters to provide a complete 4×4 transformation matrix capable of co-registering the two coordinate spaces.

Navigation system 105 can then use the transformation matrix to reformat the x-ray image being displayed so that the slice of tissue being displayed is in the same plane and in the same orientation as the field of view of the ultrasound probe of ultrasound imaging system 150. Matched ultrasound and x-ray images may then be displayed side by side, or directly overlaid in a single image viewing frame. In some embodiments, navigation system 105 can display additional x-ray images in separate frames or positions on a display screen. For example, the x-ray image can be displayed with a graphical representation of the field of view of ultrasound imaging system 150 wherein the graphical representation of the field of view is shown slicing through a 3D representation of the x-ray image. In other embodiments annotations can be additionally displayed, these annotations representing, for example, the position of instruments imaged by ultrasound imaging system 150, such as biopsy needles, guidance wires, imaging probes or other similar devices.

In other embodiments, the ultrasound image being displayed by ultrasound imaging system 150 can be superimposed on the slice of the x-ray image being displayed by navigation system 150 so that a user can view both the x-ray and ultrasound images simultaneously, overlaid on the same display. In some embodiments, navigation system 105 can enhance certain aspects of the super imposed ultrasound or x-ray images to increase the quality of the resulting combined image.

An exemplary method and system which may be used to navigate between a three dimensional image data set and an ultrasound feed, and to align coordinate systems to enable display of common reference points is described in further detail in U.S. Patent Publication No. 2012/0150034, titled "System and Method for Fusing Three Dimensional Image Data from a Plurality of Different Imaging Systems for Use in Diagnostic Imaging," which is hereby incorporated by reference in its entirety. Additional details may also be found in U.S. Patent Publication No. 2011/0134113, titled "Systems and methods for tracking positions between imaging modalities and transforming a displayed three-dimensional image corresponding to a position and orientation of a probe," which is hereby incorporated by reference in its entirety. In addition, while the system 100 is generally described as having an x-ray image acquisition system 101, in some examples the system 100 may have a magnetic resonance imaging (MRI) system in place of, or in addition to, the x-ray image acquisition system 101. Further, while the system 100 is generally described as having an ultrasound imaging system 150, in some examples the system 100 may have an optical and/or thermal imaging system in place of, or in addition to, the ultrasound imaging system 150. In some examples, the optical and/or thermal imaging system is incorporated in to the x-ray image acquisition system 101.

Figure 1B:
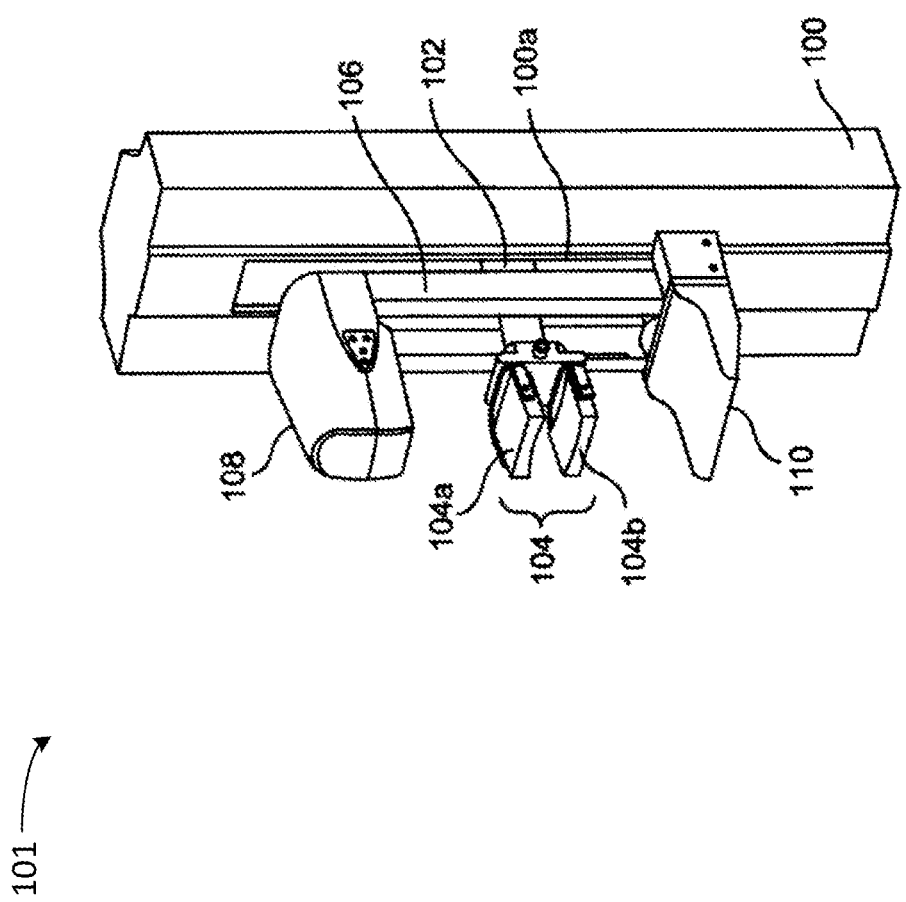
FIG. 1B depicts a perspective view of a portion of an upright breast x-ray imaging system.
Figure 1C:
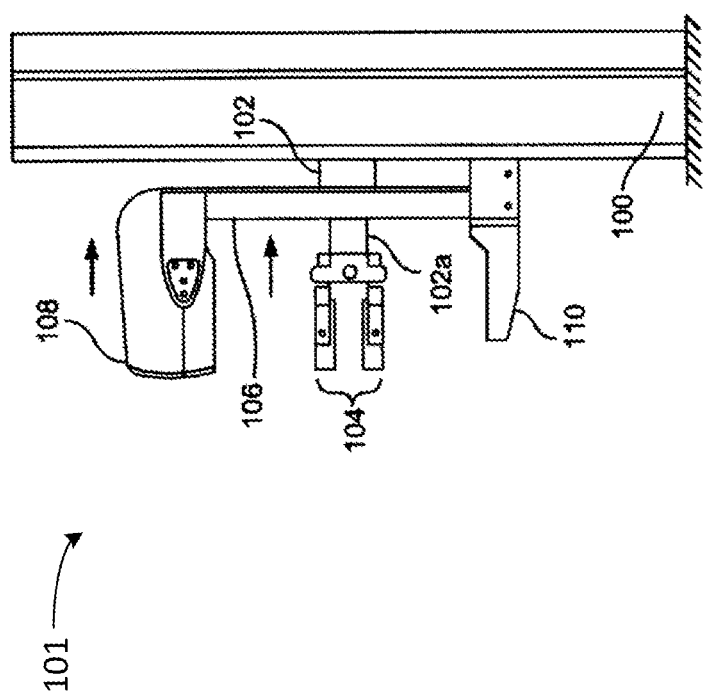
FIG. 1C is a side elevation of the system of FIG. 1B.
Figure 1D:
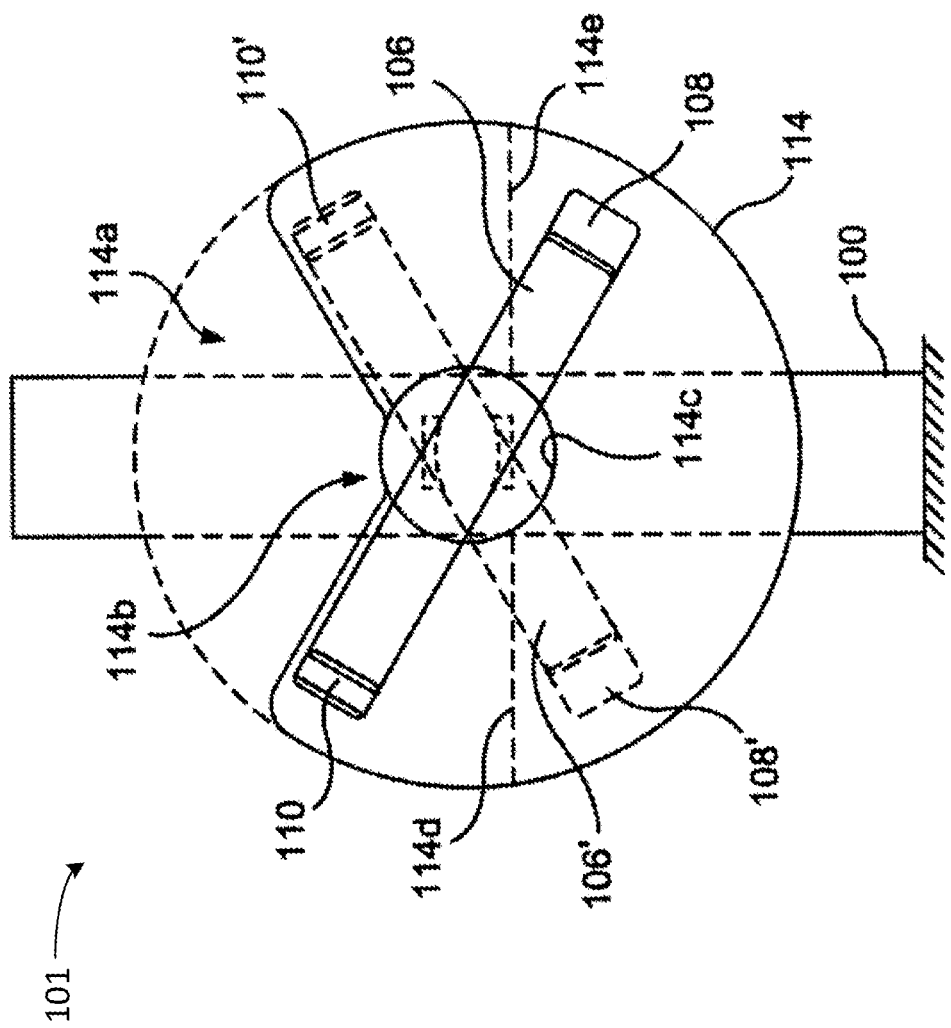
FIG. 1D is a front elevation illustrating a patient shield for a system similar to that seen in FIGS. 1B and 1C.

FIGS. 1B and 1C illustrate portions of a non-limiting example of a multi-mode breast x-ray imaging system operable in a CT mode but also configured to selectively operate in a tomosynthesis mode including a wide angle tomosynthesis mode and a narrow angle tomosynthesis mode, and in a mammography mode. For clarity of illustration, a patient shield for use in the CT mode is omitted from FIGS. 1B and 1C but examples are illustrated in FIGS. 1D and E. A support column 100 is secured to a floor and houses a motorized mechanism for raising and lowering a horizontally extending axle 102, which protrudes through an opening 100a in column 100, and for rotating axle 102 about its central axis. Axle 102 in turn supports a coaxial axle 102a that can rotate with or independently of axle 102. Axle 102 supports a breast immobilization unit comprising an upper plate 104a and a lower plate 104b such that each plate can move up and down along the long dimension of support 100 together with axles 102 and 102a, at least one of the plates can move toward the other, and unit 104 can rotate about the common central axis of axles 102 and 102a. In addition, axle 102 supports a gantry 106 for two types of motorized movement: rotation about the central axis of axle 102, and motion relative to axle 102 along the length of gantry 106. Gantry 106 carries at one end an x-ray source such as a shrouded x-ray tube generally indicated at 108, and at the other end a receptor housing 110 enclosing an imaging x-ray detector or receptor 112.

When operating in a CT mode, the system of FIGS. 1B and 1C immobilizes a patient's breast between plates 104a and 104b. To this end, unit 104 is raised or lowered together with axle 102 to the height of the breast while the patient is upright, e.g., standing or sitting. The patient leans toward unit 104 from the left side of the system as seen in FIG. 1C, and a health professional, typically an x-ray technician, adjusts the breast between plates 104a and 104b while pulling tissue to the right in FIG. 1C and moving at least one of plates 104a and 104b toward the other to immobilize the breast and keep it in place, preferably with as much as practicable of the breast tissue being inside unit 104. In the course of taking x-ray measurements representing real projection x-ray images, from which to reconstruct images of respective breast slices, gantry 106 rotates about the central axis of axle 102 while the breast remains immobilized in unit 104. Imaging receptor 112 inside housing 110 remains fixed relative to x-ray tube 108 during the rotation of gantry 106. A pyramid shaped beam of x-rays from tube 108 traverses the breast immobilized in unit 104 and impinges on imaging receptor 112, which in response generates a respective two-dimensional array of pixel values related to the amount of x-ray energy received for each increment of rotation at respective pixel positions in an imaging plane of the receptor. These arrays of pixel values for real projection images are delivered to and processed by a computer system to reconstruct slice images of the breast. Gantry 106 may be configured for motorized movement toward column 100, to facilitate the x-ray technician's access to the patient's breast for positioning the breast in unit 104, and away from column 100 to ensure that x-ray tube 108 and imaging receptor 112 inside housing 110 can image the appropriate breast tissue. Alternatively, gantry 106 can maintain a fixed distance from column 100, to the left of the position seen in FIG. 1C, so that the imaging x-ray beam can pass through as much as practical of the breast immobilized in unit 104, in which case there would be no need for a mechanism to vary that distance.

A unique challenge arises because of the upright position of the patient and the rotation of x-ray tube 108 and receptor housing 110 through a large angle in the CT mode of operation. As known, CT scanning typically involves a rotation of the source and receptor through an angle of 180° plus the angle subtended by the imaging x-ray beam, and preferably a rotation through a greater angle, e.g., 360°. However, if the rotation includes the 0° position of x-ray source 108 as seen in FIGS. 1B and 1C, the patient's head may be too close to x-ray source 108. Collision of rotating assemblies with the patient, and concern with such collision, can be avoided by the use of a shield separating the patient from assemblies rotating even the full 360, as discussed below in this patent specification, although depending on the design of the shield and the rotating assemblies in particular embodiments this may require the patient to arch her body such that both her head and legs are away from the system, to the left as seen in FIG. 1C. An alternative, also discussed below, is to exclude from the rotation a sector or segment around the position of x-ray source 108 seen in FIGS. 1B and 1C. As a non-limiting example, if the position of x-ray tube 108 seen in FIGS. 1B and 1C is designated the 0° position, then the rotation for CT imaging excludes positions of x-ray source 108 in the 90° sector or segment between 45° and 315°, or in the 120° sector or segment between 60° and 300°, or in some other sector or segment that is sufficient to clear the patient's head position while taking x-ray CT data over a sufficient angle of rotation for the reconstruction of high quality slice images. While the rotation of x-ray tube 108 and receptor housing 110 still has to clear the lower part of the patient's body, it is generally easier for a patient to keep the lower part of her body away from the rotating components, to the left as seen in FIG. 2 (and preferably behind a shield), than to arch back her head and shoulders.

Figure 1E:
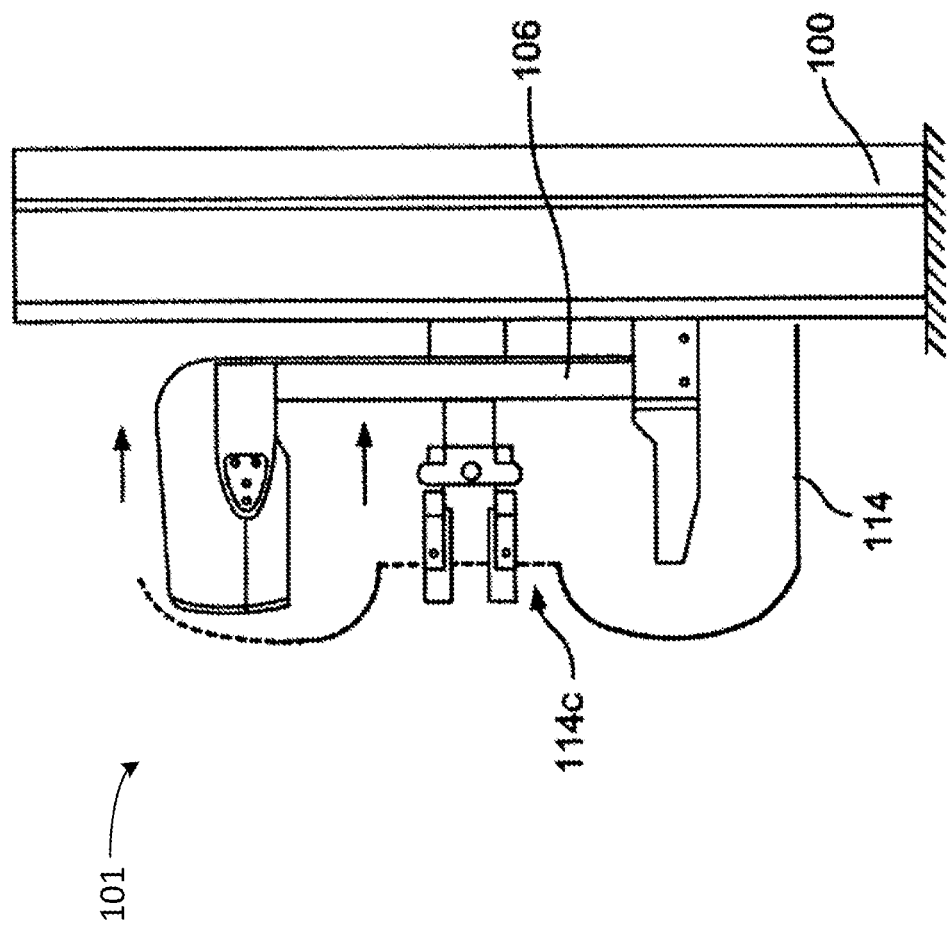
FIG. 1E is a side elevation that is the same as FIG. 1C but illustrates a patient shield.
Figure 4:
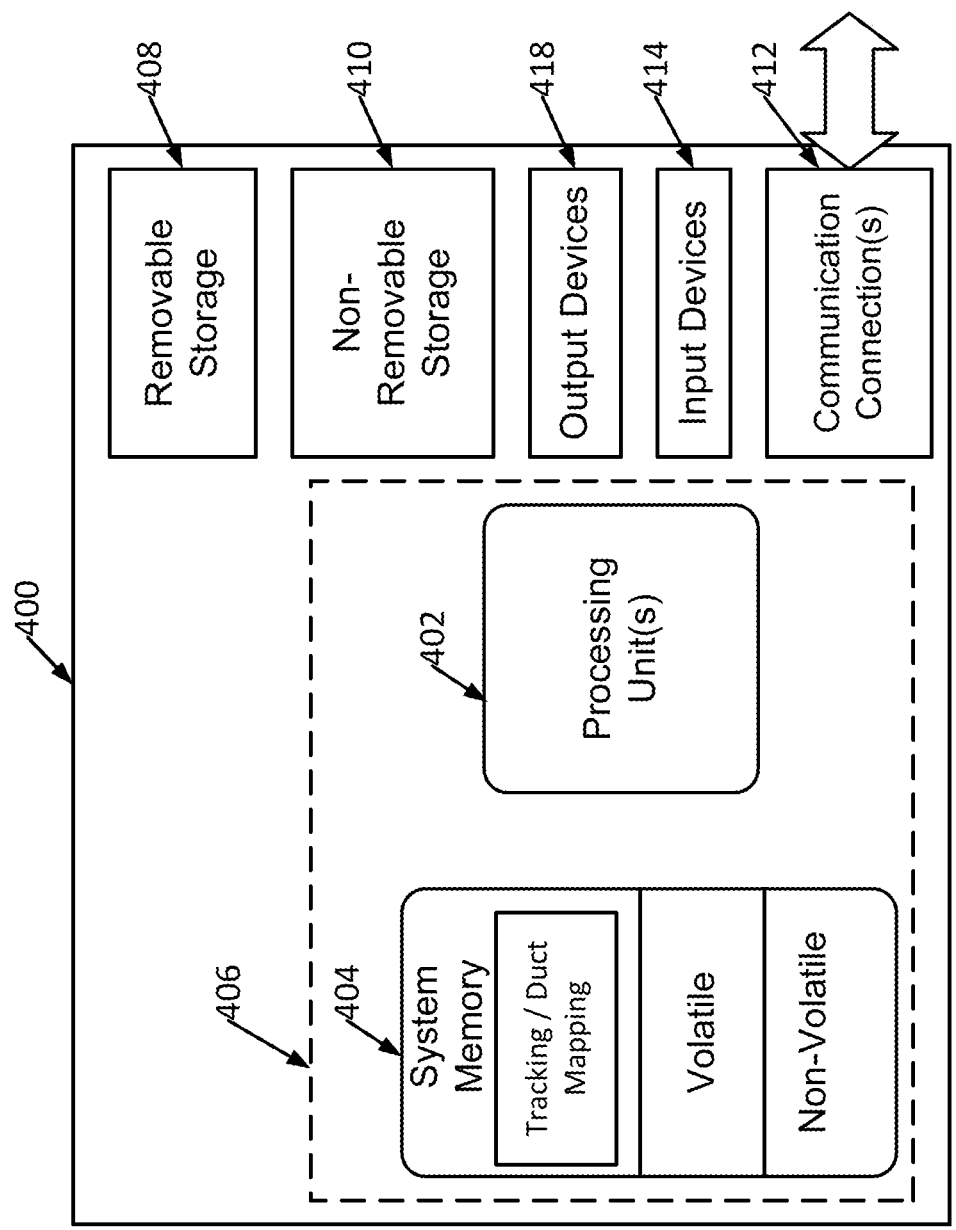
FIG. 4 illustrates one example of a suitable operating environment in which one or more of the present examples can be implemented.

An example of such a shield is illustrated in FIGS. 1D and 1E. FIG. 4 is a side elevation that is otherwise the same as FIG. 1C but additionally illustrates a patient shield 114 having a central opening 114c. Shield 114 may be completely circular in front elevation, as illustrated by the circle that includes an arc in broken line in FIG. 1D, in front elevation. In that case, gantry 106 can rotate through a complete circle in the CT mode. As an alternative, shield 114 can leave open a sector or segment 114a illustrated in FIG. 1D as the area below the broken line arc and between the solids line of shield 114. In that case, gantry 106 can rotate in the CT mode only through an angle that is less than 360°, but the patient can have space for her head and perhaps a shoulder and an arm in the V-shaped cutout 114b of shield 114, for a more comfortable body posture. Specifically, as illustrated in FIG. 1D, gantry 106 can rotate only within the portion of shield 114 that is outside V-shaped cutout 114b. One of the possible positions of gantry 106 and tube 108 and receptor housing 110 is shown in solid lines. Another possible position is shown in broken lines, and designated as gantry 106', carrying x-ray source 108' and receptor housing 110'. FIG. 1E illustrates a possible shape of shield 114 in side elevation.

Figure 1F:
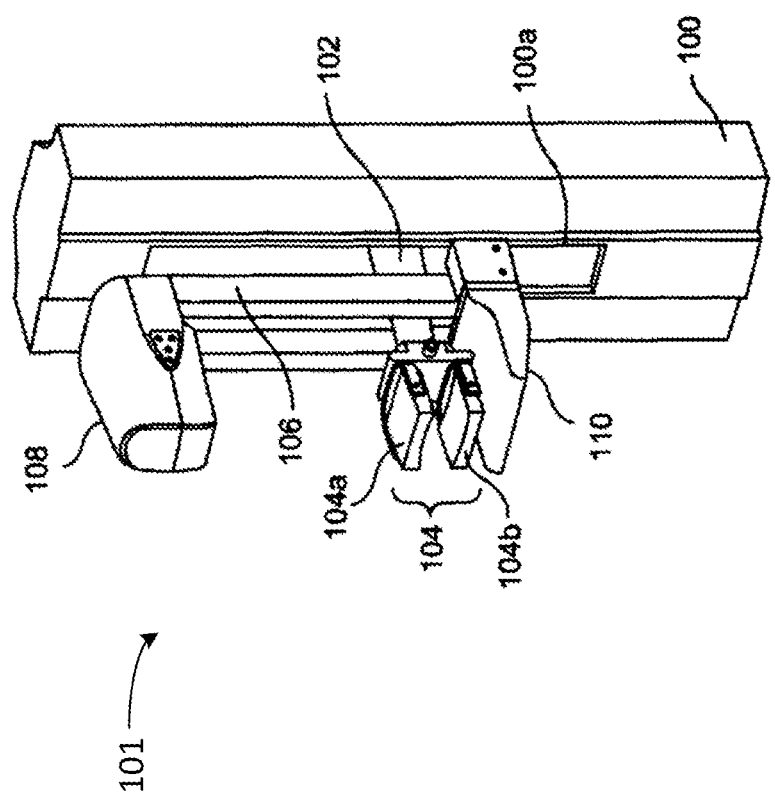
FIGS. 1F and 1G are similar to FIGS. 1B and 1D, respectively, but illustrate the system as used in a tomosynthesis mode or a mammography mode and shows a gantry that is spaced further from a support column than in FIGS. 1C and 1E.
Figure 1G:
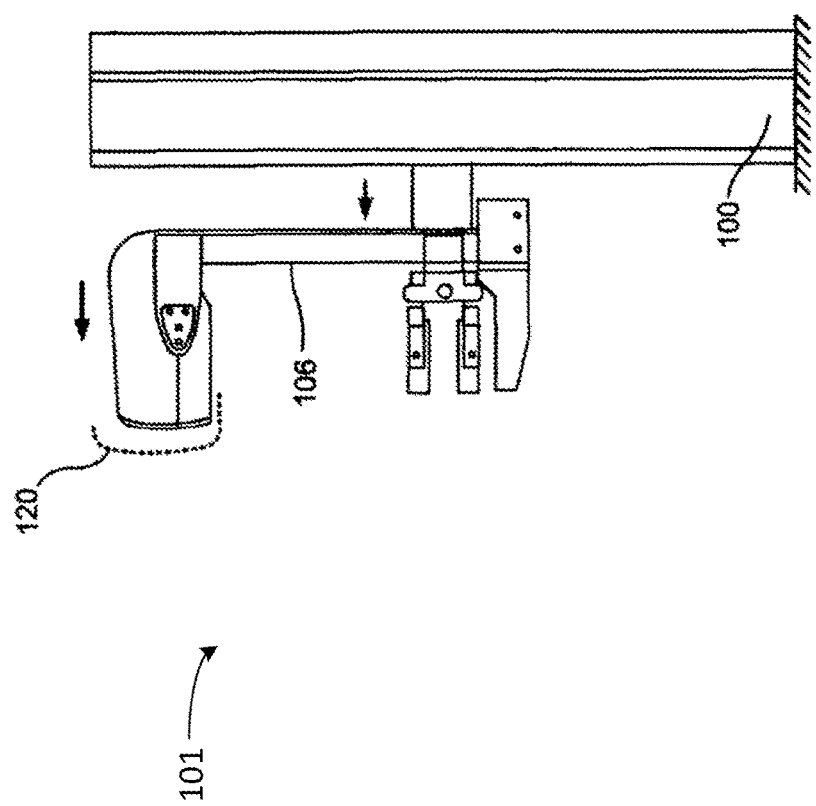
Figure 1H:
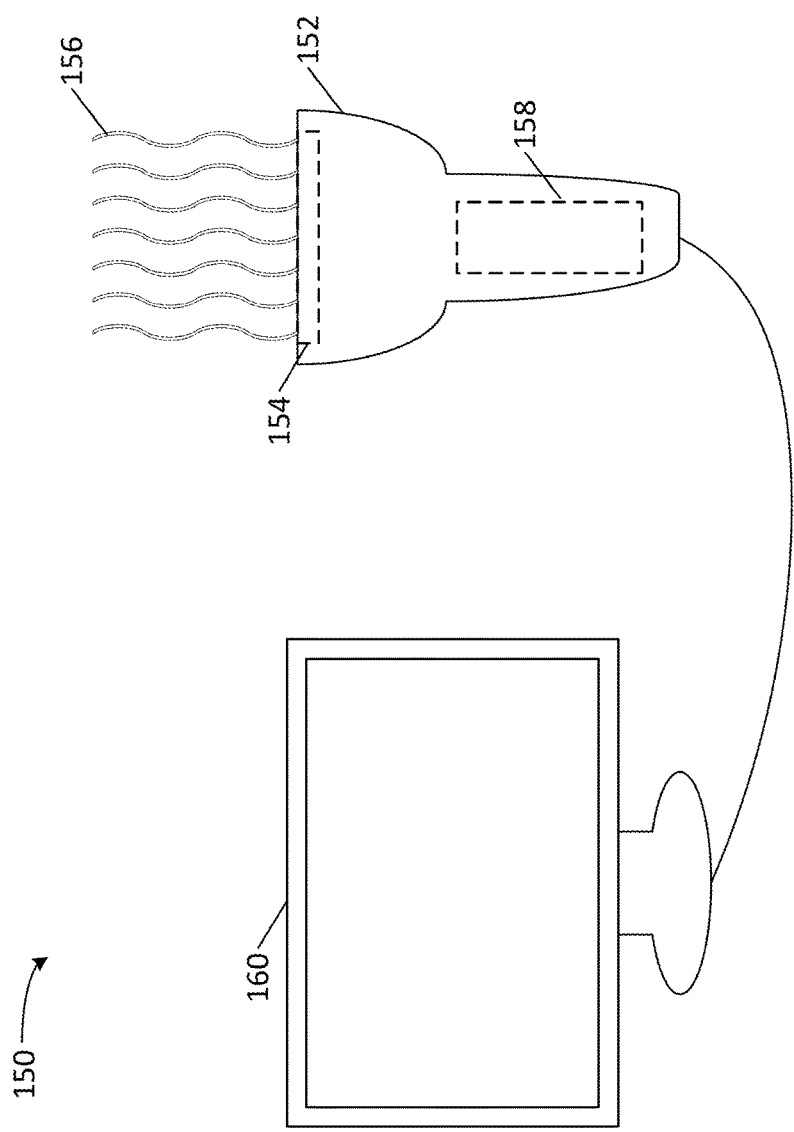
FIG. 1H depicts an example of an ultrasound imaging system.
Figure 11:
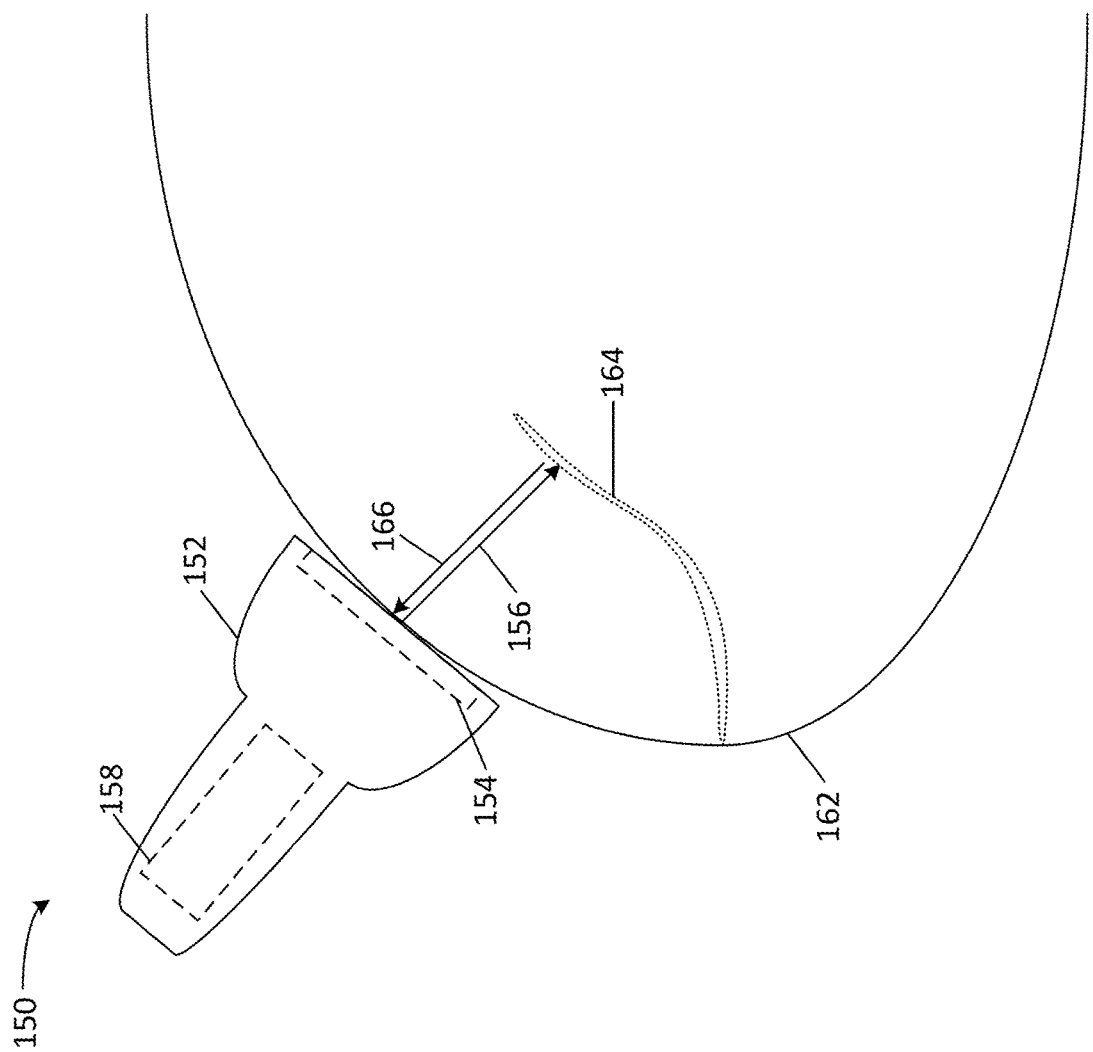

Use of the system in a tomosynthesis mode is illustrated in FIGS. 1F and 1G, which are otherwise the same as FIGS. 1A and B respectively, except that gantry 106 is in a different position relative to breast immobilization unit 104 and axle 102 and column 100, and no shield 114 is shown. In particular, x-ray source 108 is further from unit 104 and column 100, and receptor housing 110 is closer to unit 104. In the tomosynthesis mode, the patient's breast also is immobilized between plates 104a and 104b, which remain in place during imaging. In one example, x-ray tube 108 and receptor housing 110 may undergo a rotation about the immobilized breast that is similar to that in the CT mode operation but is through a smaller angle. A respective two-dimensional projection image Tp taken for each increment of rotation while x-ray tube 108 and imaging receptor 112 inside housing 110 rotate as a unit, fixed with respect to each other, as in the CT mode or as illustrated in principle in commonly assigned U.S. Pat. No. 7,123,684, the disclosure of which is hereby incorporated by reference herein in its entirety. Alternatively, the motions of x-ray tube 108 and receptor 112 relative to the immobilized breast can be as in said system offered under the trade name Selenia® Dimensions' of the common assignee, certain aspect of which are described in commonly owned U.S. Pat. No. 7,616,801, the disclosure of which is hereby incorporated by reference herein in its entirety. In this alternative case, x-ray tube rotates about the central axis of axle 102, but receptor housing 110 remains in place while imaging receptor 112 rotates or pivots inside housing 110 about an axis that typically passes through the image plane of the receptor, is parallel to the central axis of axle 102, and bisects imaging receptor 112. The rotation or pivoting of receptor 112 typically is through a smaller angle than the rotation angle of x-ray tube 108, calculated so that a normal to the imaging plane of receptor 112 can continue pointing at or close to the focal spot in x-ray tube 108 from which the imaging x-ray beam is emitted, and so that the beam continues to illuminate all or most of the imaging surface of receptor 112.

In one example of tomosynthesis mode operation, x-ray tube 108 rotates through an arc of about ±15° while imaging receptor rotates or pivots through about ±5° about the horizontal axis that bisects its imaging surface. During this motion, plural projection images RP are taken, such as 20 or 21 images, at regular increments of rotation angle. The central angle of the ±15° arc of x-ray source 108 rotation can be the 0° angle, i.e., the position of the x-ray source 108 seen in FIGS. 5 and 6, or some other angle, e.g., the angle for the x-ray source position typical for MLO imaging in conventional mammography. In the tomosynthesis mode, the breast may be immobilized in unit 104 but, alternatively, lower plate 104b may be removed so that the breast is supported between the upper surface of receptor housing 110 and upper plate 104a, in a manner analogous to the way the breast is immobilized in said system offered under the trade name Selenia®. In the tomosynthesis mode, greater degree of breast compression can be used under operator control than in the CT mode. The same concave plates 104a and 104b can be used, or generally flat plates can be substituted, or a single compression paddle can be used while the breast is supported by the upper surface of receptor housing 110, as used in said system offered under the Selenia® trade name.

When operating in a tomosynthesis mode, the system of FIGS. 1F and 1G provides multiple choices of that mode, selectable by an operator, for example a narrow angle mode and a wide angle mode. In the narrow angle tomosynthesis mode, x-ray source 108 rotates around unit 104 and the patient's breast immobilized therein through an angle such as ±15°, while in the wide angle tomosynthesis mode x-ray tube 108 rotates through an angle such as in the range of about ±15° to ±60°. The wide angle mode may involve taking the same number of projection images RP as the narrow angle mode, or a greater number. As a non-limiting example, if the narrow angle mode involves taking a total or 20 or 21 tomosynthesis projection images RP as x-ray source 108 moves through its arc around the breast, the wide angle mode may involve taking the same number of images RP or a greater number, such as 40 or 60 or some other number, typically at regular angular increments. The examples of angles of rotation of x-ray source 108 are not limiting. The important point is to provide multiple modes of tomosynthesis operations, where one mode involves x-ray source rotation through a greater angle around the breast than another tomosynthesis mode. Additional details regarding the structure and operation of image system of FIGS. 1B-1G are provided in U.S. Pat. No. 8,787,522, the disclosure of which is hereby incorporated by reference herein in its entirety. The methods and systems described herein may be implemented in digital breast tomosynthesis (DBT) procedures as well as multi-modality imaging (MMI) procedures. MMI procedures generally refers to the use of a combination of different imaging modes or techniques, such as DBT acquisitions with varying dosage levels and/or angular coverage, computerized tomography (CT) of a compressed breast, and/or a combination of the two.

In some examples, the system 101 may also include one or more optical and/or thermal imaging devices, such as digital cameras. The optical and/or thermal imaging devices may be mounted or incorporated in the gantry 106. In such examples, the optical and/or thermal imaging devices may be mounted or incorporated near, or proximate to, the x-ray tube 108. By incorporating the optical and/or thermal imaging devices into the gantry 106, optical and thermal imaging data of the breast may be captured. The optical and thermal imaging data of the breast may be captured concurrently with the capture of the tomosynthesis and/or mammogram images. A map of the structures, such as ducts, of the breast and, in some examples, a vascular map of the breast may be generated from the optical and/or thermal imaging data. The optical and/or thermal imaging data may also be used to map the structures of the breast in combination with, or as a substitute for, ultrasound imaging data. The optical and/or thermal imaging data may also be co-registered with the x-ray data captured by the system 101. In some examples, the co-registration of the optical and/or thermal imaging data with the x-ray data is simplified due to the optical and/or thermal imaging devices being attached to the gantry 106 near the x-ray tube 108. In such examples, the optical and/or thermal imaging devices move with the x-ray tube 108.

FIG. 1H depicts an example of an ultrasound imaging system 150. The ultrasound localization system 150 includes an ultrasound probe 152 that includes an ultrasonic transducer 154. The ultrasonic transducer 154 is configured to emit an array of ultrasonic sound waves 156. The ultrasonic transducer 154 converts an electrical signal into ultrasonic sound waves 156. The ultrasonic transducer 154 may also be configured to detect ultrasonic sound waves, such as ultrasonic sound waves that have been reflected from internal portions of a patient, such as ducts within a breast. In some examples, the ultrasonic transducer 154 may incorporate a capacitive transducer and/or a piezoelectric transducer, as well as other suitable transducing technology.

The ultrasonic transducer 154 is also operatively connected (e.g., wired or wirelessly) to a display 160. The display 160 may be a part of a computing system, including processors and memory configured to produce and analyze ultrasound images. Further discussion of a suitable computing system is provided below with reference to FIG. 5. The display 160 is configured to display ultrasound images based on an ultrasound imaging of a patient. The ultrasound imaging performed in the ultrasound localization system 150 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized. For example, the ultrasound probe may operate in a 3D ultrasound mode that acquires ultrasound image data from a plurality of angles relative to the breast to build a 3D model of the breast. In some examples, ultrasound images may not be displayed during the acquisition process. Rather, the ultrasound data is acquired and a 3D model of the breast is generated without B-mode images being displayed.

The ultrasound probe 152 may also include a probe localization transceiver 158. The probe localization transceiver 158 is a transceiver that emits a signal providing localization information for the ultrasound probe 152. The probe localization transceiver 158 may include a radio frequency identification (RFID) chip or device for sending and receiving information as well as accelerometers, gyroscopic devices, or other sensors that are able to provide orientation information. For instance, the signal emitted by the probe localization transceiver 158 may be processed to determine the orientation or location of the ultrasound probe 152. The orientation and location of the ultrasound probe 152 may be determined or provided in three-dimensional components, such as Cartesian coordinates or spherical coordinates. The orientation and location of the ultrasound probe 152 may also be determined or provided relative to other items, such as an incision instrument, a marker, a magnetic direction, a normal to gravity, etc. With the orientation and location of the ultrasound probe 152, additional information can be generated and provided to the surgeon to assist in guiding the surgeon to a lesion within the patient, as described further below. While the term transceiver is used herein, the term is intended to cover both transmitters, receivers, and transceivers, along with any combination thereof. Additional details of examples of systems and components for localization and co-registration of an ultrasound probe are provided in U.S. Patent Publication No. 2012/0150034, titled "System and Method for Fusing Three Dimensional Image Data from a Plurality of Different Imaging Systems for Use in Diagnostic Imaging," which is hereby incorporated by reference in its entirety.

FIG. 1I depicts an example of the ultrasound imaging system 100 in use with breast 162 of a patient. The ultrasound probe 152 is in contact with a portion of the breast 162. In the position depicted in FIG. 1B, the ultrasound probe 152 is being used to image a structure of the breast. In the example depicted, the ultrasound probe 152 is being used to image a duct 164 of the breast 162. To image duct 164, the ultrasonic transducer 154 emits an array of ultrasonic sound waves 156 into the interior of the breast 162. A portion of the ultrasonic sound waves 156 are reflected off internal components of the breast, such as the duct 164 when the duct is in the field of view, and return to the ultrasound probe 152 as reflected ultrasonic sound waves 166. The reflected ultrasonic sound waves 166 may be detected by the ultrasonic transducer 154. For instance, the ultrasonic transducer 154 receives the reflected ultrasonic sound waves 166 and converts the reflected ultrasonic sound waves 166 into an electric signal that can be processed and analyzed to generate ultrasound image data on display 160. The depth of the duct 164 or other objects in an imaging plane may be determined from the time between a pulse of ultrasonic waves 156 being emitted from the ultrasound prove 152 and the reflected ultrasonic waves 166 being detected by the ultrasonic probe 152. For instance, the speed of sound is well-known and the effects of the speed of sound based on soft tissue are also determinable. Accordingly, based on the time of flight of the ultrasonic waves 156 (more specifically, half the time of flight), the depth of the object within an ultrasound image may be determined. Other corrections or methods for determining object depth, such as compensating for refraction and variant speed of waves through tissue, may also be implemented. Those having skill in the art will understand further details of depth measurements in medical ultrasound imaging technology. Such depth measurements and determinations may be used to build a 3D model of the breast 162, and more specifically, a 3D model of the ducts 164 of the breast 162. For instance, a whole breast 162 may be imaged with the ultrasound probe 152. By imaging the whole breast 162 with 3D ultrasound techniques, 3D models of different structures, such as ducts 164, may be generated.

In addition, multiple frequencies or modes of ultrasound techniques may be utilized. For instance, real time and concurrent transmit and receive multiplexing of localization frequencies as well as imaging frequencies and capture frequencies may be implemented. Utilization of these capabilities provide information to co-register or fuse multiple data sets from the ultrasound techniques to allow for visualization of ducts 164 and other medical images on the display 160. The imaging frequencies and capture sequences may include B-mode imaging (with or without compounding), Doppler modes (e.g., color, duplex), harmonic mode, shearwave and other elastography modes, and contrast-enhanced ultrasound, among other imaging modes and techniques.

Figure 2A:
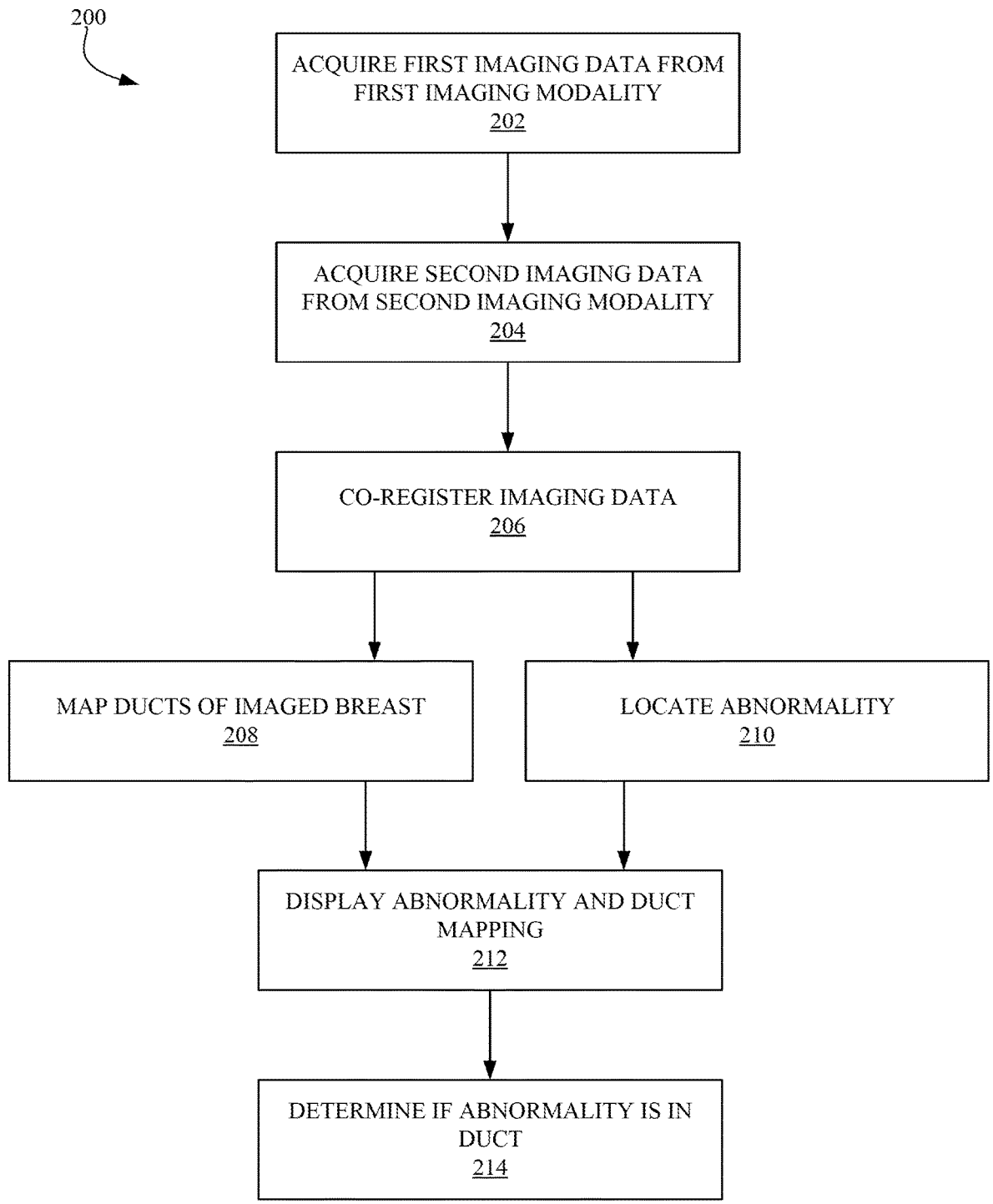
FIG. 2A depicts a method for localization of an abnormality within a breast.

FIG. 2A depicts an example method 200 for locating an abnormality within a breast. At operation 202, first imaging data for a breast from a first imaging modality is acquired or received, which may be an x-ray-based imaging modality and/or a magnetic resonance imaging (MRI) modality. The first imaging data may be two-dimensional imaging data or three-dimensional imaging data. In some examples, the first imaging data may be acquired from a tomosynthesis imaging system and/or a computed tomography system. In such an example, the first imaging data may be 3D imaging data. In other examples, the first imaging data may be 2D imaging data, such as mammography imaging data. At operation 204, second imaging data is acquired for the breast from a second imaging modality. The second imaging modality may be an ultrasound imaging modality. In other examples, the second imaging modality may be an optical and/or thermal imaging modality. In some examples, the second imaging modality may include both the ultrasound imaging modality and the optical and/or thermal imaging modality. The first imaging data and the second imaging data may then be co-registered at operation 206, such that the first imaging data from the first imaging modality and the second image data from the second imaging modality share a common coordinate space. Co-registering the imaging data from the different modalities at operation 206 may be accomplished through any of the means discussed above.

At operation 208, a plurality of ducts for the breast are mapped to generate a mapping of the plurality of ducts. The mapping of the breast ducts may be generated from the second imaging data, such as ultrasound imaging data, acquired at operation 204. The mapping of the breast ducts may be 3D mapping or a plurality of 2D mappings of the breast ducts and may include a mapping of all the ducts in the breast. In some instances, the mapping of the breast ducts may achieved through artificial-intelligence image analysis techniques. Such image analysis techniques may analyze the second image data to identify ductal structures within the image data for the imaged breast. In some examples, the non-ductal tissue (i.e., the tissue of the breast other than the ducts) may be removed from the imaging data to form the mapping of the breast ducts. The image analysis techniques may be trained using a dataset of image data where ductal structures have been previously identified, such as by manual identification. Once the image analysis techniques have been trained, the image analysis techniques are able to identify ducts within image data. Once the ducts are identified, the mapping of the breast ducts is generated.

At operation 210, an abnormality is located or identified in the first imaging data from the first modality that was received or acquired in operation 202 and/or the second imaging data from the second imaging modality that was received or acquired in operation 204. In examples where the first imaging data is x-ray data in the form of tomography or mammography image data, the abnormality may appear brighter in the image data, such as when the abnormality is a calcification. For example, pixels in the image data having a higher value (i.e., brighter) may correspond to an abnormality. The abnormality may be identified through the use of image analysis techniques that analyze the image data based on pixel values or the patterns of pixels. The image analysis techniques may be performed in the spatial, transform, or frequency domains. For example, image analysis techniques in the spatial domain generally operate based on the pixel values in the imaging data. Image analysis techniques within the transform or frequency domains generally operate based on mathematical transforms, such as a Fourier or Laplace transform, of the pixel data from imaging data. For instance, in the frequency domain, the image analysis techniques may be based on a rate of change of pixel values within the spatial domain. In other examples, an abnormality may be identified through the assistance of a medical professional. For instance, locating the abnormality may include the medical professional selecting the abnormality on a screen displaying the imaging data.

At operation 212, at least a portion of the mapping of the breast ducts generated in operation 208 is displayed concurrently with in the abnormality that was located in operation 210. The concurrent display of the mapping of the breast ducts and the abnormality allows for a determination as to whether the abnormality is located inside or outside of one of the breast ducts. For example, the abnormality may be displayed as an overlay of a portion of the mapping of the plurality of ducts. Due to the first imaging data being co-registered with the second imaging data, an abnormality that is located in the first imaging data may be displayed in a mapping of the breast ducts in the proper location even though the mapping of the breast ducts was generated from the second imaging data. In some examples, imaging data displaying the abnormality maybe displayed, and a selection of a region of interest, such as a region containing the abnormality, may be selected from the displayed imaging data. Based on receiving the selection of the region of interest, a portion of the mapping of the ducts corresponding to the selected region of interest may be displayed.

At operation 214, a determination may be made as to whether the abnormality is inside or outside of a breast duct based on the mapping of the breast ducts. In one example, the determination may be made based on the concurrent display of the abnormality and the duct mapping. The determination may be made through image analysis techniques that analyze the concurrent display of the abnormality and the duct mapping to identify whether the abnormality is inside or outside of a breast duct. The determination may also be made based on the location of the abnormality and the locations of the breast ducts. For example, a location of the abnormality may be determined and represented in coordinates of the shared coordinate space between the first imaging data and the second imaging data. The structures of the ducts may also be represented in coordinates of the shared coordinate space. Accordingly, a determination may be made as to whether the location of the abnormality falls inside or outside the ducts.

Figure 2B:
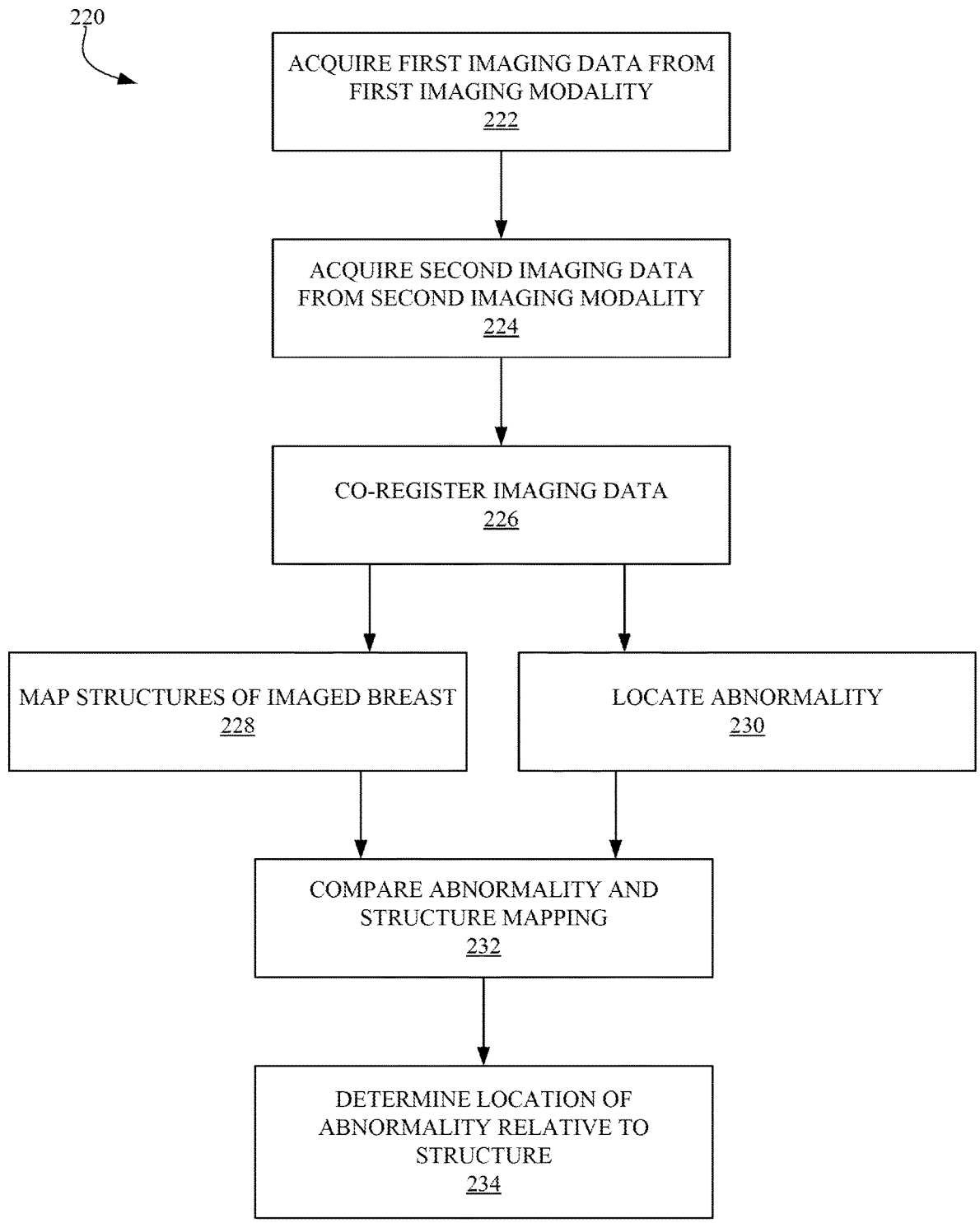
FIG. 2B depicts a method for localization of an abnormality within a breast.

FIG. 2B depicts another example method 220 for locating an abnormality within a breast. At operation 222, first imaging data for a breast from a first imaging modality is acquired or received, which may be an x-ray-based imaging modality and/or a magnetic resonance imaging (MRI) modality. The first imaging data may be two-dimensional imaging data or three-dimensional imaging data. In some examples, the first imaging data may be acquired from a tomosynthesis imaging system and/or a computed tomography system. In such an example, the first imaging data may be 3D imaging data. In other examples, the first imaging data may be 2D imaging data, such as mammography imaging data. At operation 224, second imaging data is acquired for the breast from a second imaging modality. The second imaging modality may be an ultrasound imaging modality. The second imaging data may include 3D ultrasound data of a whole breast. For instance, during an ultrasound imaging procedure, the ultrasound imaging system may acquire a series of 2D slice and stitches and/or stacks the 2D slices together to form a set of 3D data or a 3D ultrasound volume of the breast. In other examples, the second imaging modality may be an optical and/or thermal imaging modality. In some examples, the second imaging modality may include both the ultrasound imaging modality and the optical and/or thermal imaging modality. The first imaging data and the second imaging data may then be co-registered at operation 226, such that the first imaging data from the first imaging modality and the second image data from the second imaging modality share a common coordinate space. Co-registering the imaging data from the different modalities at operation 226 may be accomplished through any of the means discussed above.

At operation 228, one or more structures of the breast are mapped or modeled based on the first imaging data and/or the second imaging data. For example, the mapping or modeling of the structures may be generated from the second imaging data, such as ultrasound imaging data, acquired at operation 224. The mapping or modeling of the breast structures may be a 3D model or mapping or a 2D model of mapping. The mapping or model may also be for the whole breast. In some examples, the mapping or modeling of the breast structures may be achieved through artificial-intelligence image analysis techniques. Such image analysis techniques may analyze the first imaging data and/or the second imaging data to identify particular structures within the breast. For example, the structures may be ducts, lobules, Cooper's ligaments, dense tissue, fat, skin, vascular structures and/or lymph nodes. The particular structure(s) that are modeled may be selected by a clinician or automatically set by the imaging system. In addition, multiple models or mappings may be generated. For instance, a first model or mapping of ducts may be generated and a second model or mapping for lobules may be generated. In some examples, the tissue of the breast that is not the structure being modeled (such as non-ductal tissue) may be removed from the imaging data when generating the mapping or modeling of the breast structure(s). The image analysis techniques may be trained using a dataset of image data where the desired structures have been previously identified, such as by manual identification. Once the image analysis techniques have been trained, the image analysis techniques are able to identify ducts within image data. For example, the echogenicity of different structures as well as patterns and textures of those structures allows for the structures to be identified within the image data. Once the structures are identified, the mapping or model of the structures is generated.

At operation 230, an abnormality is located or identified in the first imaging data from the first modality that was received or acquired in operation 222 and/or the second imaging data from the second imaging modality that was received or acquired in operation 224. In examples where the first imaging data is x-ray data in the form of tomography or mammography image data, the abnormality may appear brighter in the image data, such as when the abnormality is a calcification. For example, pixels in the image data having a higher value (i.e., brighter) may correspond to an abnormality. The abnormality may be identified through the use of image analysis techniques that analyze the image data based on pixel values or the patterns of pixels. The image analysis techniques may be performed in the spatial, transform, or frequency domains. For example, image analysis techniques in the spatial domain generally operate based on the pixel values in the imaging data. Image analysis techniques within the transform or frequency domains generally operate based on mathematical transforms, such as a Fourier or Laplace transform, of the pixel data from imaging data. For instance, in the frequency domain, the image analysis techniques may be based on a rate of change of pixel values within the spatial domain. In other examples, an abnormality may be identified through the assistance of a medical professional. Locating the abnormality may include the medical professional selecting the abnormality on a screen displaying the imaging data.

At operation 232, the abnormality that was located in operation 230 is compared to the mapping or model of the breast structures generated in operation 228. The comparison of the abnormality to the mapping or model may include displaying at least a portion of a visual representation of the mapping concurrently with the abnormality. The concurrent display may include an overlapped display such that the abnormality is displayed within the mapping or model of the breast structure. In other examples, the comparison may include a mathematical or numerical comparison. For instance, the locations of the structures may be defined mathematically in the mapping or model. Similarly, the location of the abnormality may be also be defined mathematically. At operation 234, the location of abnormality relative to the mapped or modeled structure(s) is determined. For example, a determination may be made as to whether the abnormality is within the duct of a breast or within or attached to a lobule. Such information can provide additional information for identifying the type or risk of the abnormality. The determined relative location may be displayed or presented in a variety of manners. For instance, the relative location may be displayed as a distance from the center or perimeter of the abnormality to the center or perimeter of one or more of the modeled structures.

Figure 3A:
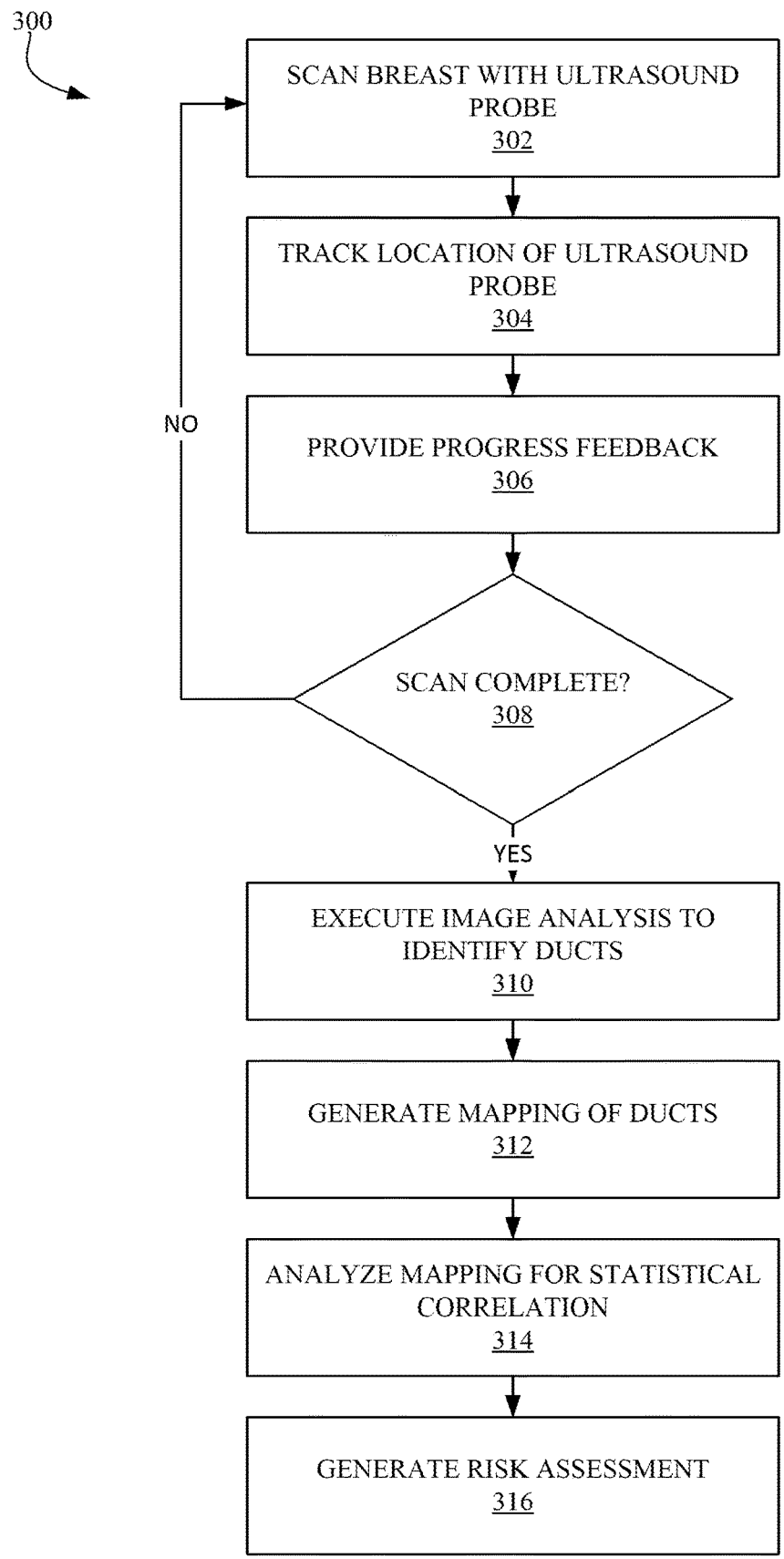
FIG. 3A depicts an example method for imaging a breast and generating a risk assessment.

FIG. 3A depicts an example method 300 for imaging a breast and generating a risk assessment. At operation 302 the breast is scanned with an ultrasound probe. For instance, an ultrasound technician may contact the probe to the surface of the breast and begin scanning the breast. At operation 304, the location of the ultrasound probe is tracked during the scan of the breast. Tracking the location of the ultrasound probe may also include tracking the orientation of the probe as well. By tracking the location and orientation of the ultrasound probe, a 3D mapping of the breast ducts may later be generated and the image data acquired from the ultrasound imaging may be co-registered with imaging data from another imaging modality, such as x-ray imaging data. Feedback regarding progress of the scan may also be provided during the scan at operation 306. The feedback may be visual feedback that indicates to the ultrasound technician whether the breast has been fully imaged. For example, to map all the ducts in the breast, the entire breast may need to imaged, or at least the portion of the breast that includes ducts. The visual feedback may be in the form of a graphical user interface element that updates during the scan. The graphical user interface element may be a circle or ellipse that is generally representative of the breast. As portions of the breast are scanned, the equivalent portions of the circle will change color or appear shaded to indicate that the corresponding portion of the breast has been scanned. As such, the ultrasound technician is able to see what portions of the breast still need to be scanned. Other visual indicators that indicate similar information may also be used. At operation 308, a determination is made as to whether the scan has completed. The determination may be based on the ultrasound technician providing input indicating the scan is complete. In other examples, the system may make the determination based on the tracking of the ultrasound probe and the progress feedback. For instance, if the progress feedback indicates that the breast has not been fully or entirely scanned, the determination at operation 308 is that the scan is not complete. If it is determined that the scan is not complete at operation 308, an alert may be provided to the ultrasound technician to continue scanning until the scanning is complete. In addition, the method 300 flows back to operation 302 where the ultrasound scanning continues until the full breast is scanned. If it is determined at operation 308 that the scan is complete, the method 300 flows to operation 310.

At operation 310, an image analysis technique is executed to identify the ducts within the breast. In some instances, the identification and mapping of the breast ducts may achieved through artificial-intelligence image analysis techniques. Such image analysis techniques may analyze image data from the ultrasound scan to identify ductal structures within the image data for the imaged breast. In some examples, the non-ductal tissue (i.e., the tissue of the breast other than the ducts) may be removed from the imaging data to generate ductal image data. The image analysis techniques may be trained using from a dataset of image data where ductal structures have been previously identified, such as by manual identification. Once the image analysis techniques have been trained, the image analysis techniques are able to identify ducts within image data.

At operation 312, a mapping of the ducts of the breast may be generated. The mapping of the ducts may be a 3D mapping of the ducts or a plurality of 2D mapping of the ducts. In some examples, the mapping of the ducts of the breast is generated from the ductal image data generated in operation 310. At operation 314, the mapping of the ducts generated in operation 312 is analyzed to determine a statistical correlation between the mapping of the ducts and data for an aggregation of ductal structures for other breasts. As discussed above, the pattern or structure of the ducts of a breast may be indicative of potential invasive cancers. As such, comparing the mapping of the ducts for a patient to prior ductal structures of patients having different types of cancers may reveal potential risk factors. As an example, data may be aggregated for a number of patients that have been diagnosed with different types of cancers. The data may include the type of cancer and a mapping of the ducts for the patient. A statistical correlation may then be determined for a current mapping of a breast to the aggregated data for prior duct mappings of other patients. Based on statistical correlation determined at operation 314, a risk assessment for the breast may be generated at operation 336. The risk assessment may indicate whether the breast is at a high or low risk for certain types of cancers. The risk assessment may also indicate whether additional diagnostic procedures, such as mammography or tomography procedures, biopsy procedures, or other diagnostic procedures should be performed.

While method 300 is generally discussed as utilizing ultrasound imaging techniques, operations 310-316 may also be performed with optical and/or thermal imaging data. For instance, optical and/or thermal imaging data may be acquired instead of, or in addition to, the ultrasound imaging data. The identification of ducts in operation 310 and the generation of the mapping of the ducts in operation 312 may then be performed based on the optical and/or thermal imaging data.

Figure 3B:
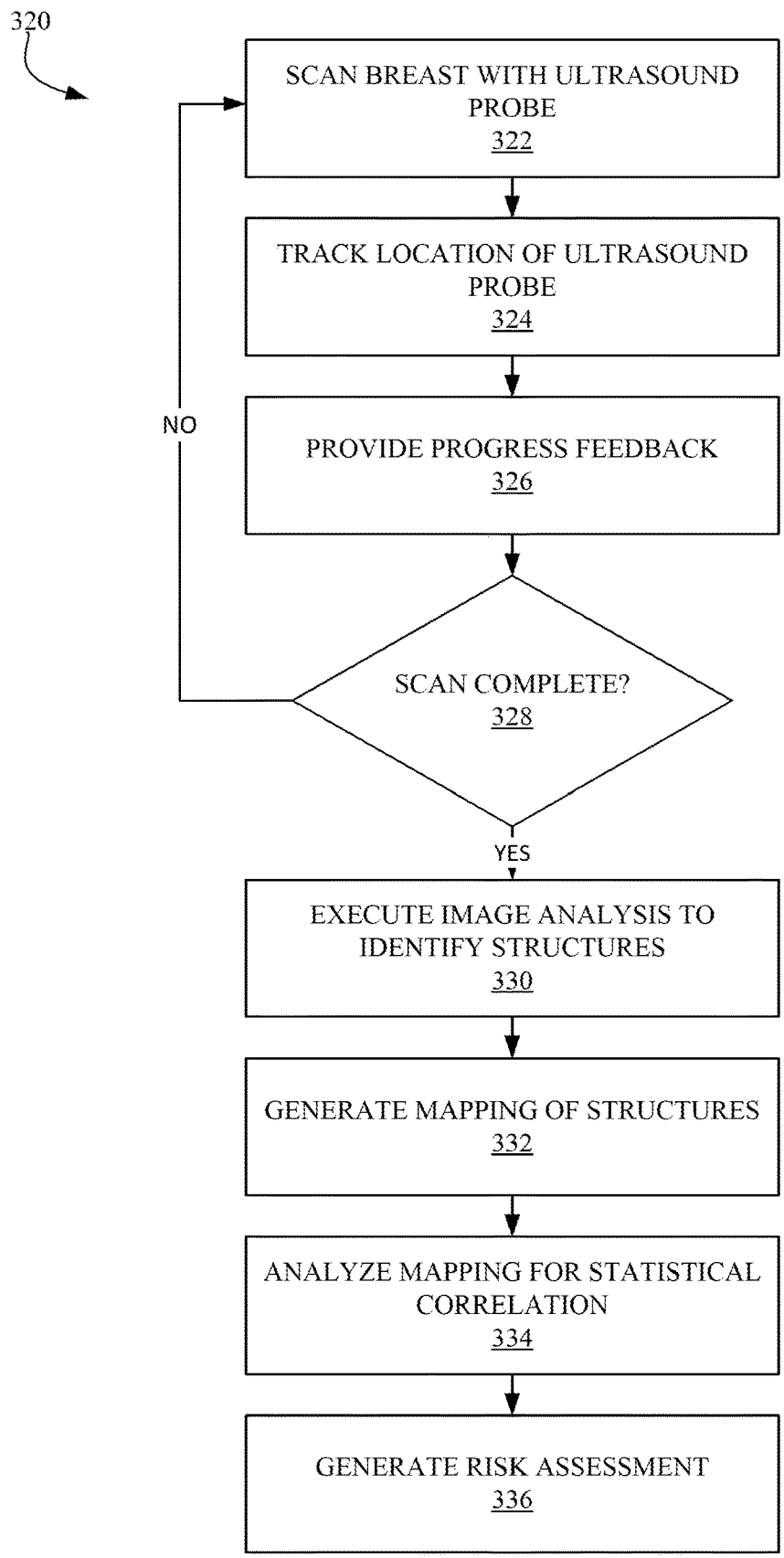
FIG. 3B depicts another example method for imaging a breast and generating a risk assessment.

FIG. 3B depicts another example method 320 for imaging a breast and generating a risk assessment. The method 320 begins with scanning of the breast with the ultrasound probe in operation 322. During the scanning of the breast, the location of the ultrasound probe is tracked at operation 324. Feedback regarding progress of the scan may also be provided during the scan at operation 326. At operation 328, a determination is made as to whether the scan has been completed. Operations 322-328 may be substantially the same as operations 302-308 in method 300 depicted in FIG. 3A.

Once the scan is complete, in operation 330, one or more anatomical structures of the breast are identified within the image data generated by the scan. In some instances, the mapping of the breast ducts may achieved through artificial-intelligence image analysis techniques. Such image analysis techniques may analyze image data from the ultrasound scan to identify the desired or selected structures within the image data for the imaged breast. The image analysis techniques may be trained from a dataset of image data where the selected or desired structures have been previously identified, such as by manual identification. Once the image analysis techniques have been trained, the image analysis techniques are able to identify the selected structures within image data.

At operation 332, a mapping or model of the selected or desired structures of the breast may be generated. The mapping or model of the structures may be a 3D mapping of the structures or a plurality of 2D mapping of the structures and may be for substantially the whole breast. In some examples, the mapping or model may be for a portion of the breast. The mapping or model of the structures of the breast may be generated from the structures identified in operation 330. At operation 334, the mapping or model of the structures generated in operation 332 is analyzed to determine and generate a risk assessment in operation 336. The analysis of the structures may include analyzing patterns within the mapping or model to extract features or values associated with the structures. For example, from the mapping or model of the structures, quantitative values for features may be extracted. In the example of a model or mapping of ducts, the number of ducts, a regularity pattern for the ducts, and/or a termination regularity for the ducts may be extracted from the mapping or model. Those extracted features or structures may then be compared to one or more thresholds, known values, or benchmarks. The analysis may also include a statistical correlation between the mapping or model of the structure(s) and data for an aggregation of the same type of structure(s) for other breasts. For instance, comparing the mapping of the structure for a patient to prior mappings of the same type of structures for patients having different types of cancers may reveal potential risk factors. As an example, data may be aggregated for a number of patients that have been diagnosed with different types of cancers. The data may include the type of cancer and a mapping of the structure for the patient. A statistical correlation may then be determined for a current mapping of a breast to the aggregated data for prior duct mappings of other patients. Based on that analysis, a risk assessment for the breast may be generated at operation 336.

The analysis of the structures may different depending on the type of structure that is being analyzed. For example, features of breast ducts that may increase a risk assessment for a patient may include features indicative of ductal ectasia (dilation), solid material or masses within a duct, an abrupt change in the caliber of the duct, and/or an abrupt termination of a duct. Such features may be extracted from a mapping or model of the ducts and/or from the imaging data itself generated during the scan. In examples where the selected or desired structure is a lobule, features that may increase a risk assessment for a patient may include features indicative of dilation of a lobule, solid material or masses within the lobule, and/or a distortion of a lobular cluster. Such features may be extracted from a mapping or model of the lobules and/or from the imaging data itself generated during the scan. In examples where the selected or desired structure is a Cooper's ligament, features that may increase a risk assessment for a patient may include distortion of a normal undulating flow, an abrupt interruption of a Cooper's ligament, and/or a thickening of the ligament. In examples where the selected or desired structure is dense tissue, features that may increase a risk assessment for a patient may include areas of prominent shadowing and/or asymmetry of the dense tissue in the breast. In examples where the selected or desired structure is fat, features that may increase a risk assessment for a patient may include a lack of homogeneity, such as stranding in normally hypoechoic fat (indicating edema), retroglandular fat (near the pectoralis muscle) stranding (suggesting tumor invasion), and/or edema or inflammation. In examples where the selected or desired structure is skin, features that may increase a risk assessment for a patient may include a thickening of the skin (such as greater than about 2 mm) and/or an interruption of a deep dermis. In examples where the selected or desired structure is a vascular structure, features that may increase a risk assessment for a patient may include a region of increased vascularity. In examples where the selected or desired structure is a lymph node, features that may increase a risk assessment for a patient may include a thickened cortex of the lymph node (such as greater than 3 mm) and/or a lack of a fatty central hilum.

Values for the above discussed features of the respective structures may be determined based on aggregated patient data. For instance, for the feature of a thickened cortex of a lymph node, the value of the thickness of a lymph node that may be indicative of a high likelihood for an abnormality may be determined based on an aggregate of lymph node mappings from patients having cancer or other abnormalities. The risk assessment may indicate whether the breast is at a high or low risk for certain types of cancers. The risk assessment may also indicate whether additional diagnostic procedures, such as mammography or tomography procedures, biopsy procedures, or other diagnostic procedures should be performed.

The methods described above may be performed by the systems described herein. For example, a system may include one or more imaging systems, such as a tomosynthesis, mammography, MRI, ultrasound, thermal, and/or optical imaging systems. One or more of those imaging systems may be operatively connected to a computing device, such as a computing device incorporating the operating environment discussed below with reference to FIG. 4. The imaging data may be received by the computing device and the computing device may then perform the operations of the methods described herein. For example, the computing device may include at least one processor and memory that is operatively connected to the at least one processor. The memory may store instructions that when executed by the at least one processor cause the system to perform the operations described herein.

FIG. 4 illustrates one example of a suitable operating environment 400 in which one or more of the present embodiments can be implemented. This operating environment may be incorporated directly into the imaging systems disclosed herein, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 400 typically includes at least one processing unit 402 and memory 404. Depending on the exact configuration and type of computing device, memory 404 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 4 by dashed line 406. Further, environment 400 can also include storage devices (removable, 408, and/or non-removable, 410) including, but not limited to, magnetic or optical disks or tape. Similarly, environment 400 can also have input device(s) 414 such as touch screens, keyboard, mouse, pen, voice input, etc., and/or output device(s) 416 such as a display, speakers, printer, etc. Also included in the environment can be one or more communication connections 412, such as LAN, WAN, point to point, Bluetooth, RF, etc.

Operating environment 400 typically includes at least some form of computer readable media. Computer readable media can be any available media that can be accessed by processing unit 402 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 400 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 400 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 400 is part of a network that stores data in remote storage media for use by the computer system 400.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. Moreover, while different examples and embodiments may be described separately, such embodiments and examples may be combined with one another in implementing the technology described herein. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for imaging a breast, the method comprising:
   receiving ultrasound image data for a breast scanned with an ultrasound probe;
   executing an artificial intelligence image analysis technique to identify one or more anatomical structures of the breast within the ultrasound image data;
   removing tissue other than the identified one or more anatomical structures from the ultrasound image data;
   generating, from the identified one or more anatomical structures, a model of the one or more structures of the breast, wherein the model comprises one of:
     a 3D mapping of the anatomical structures; and
     a plurality 2D mapping of the anatomical structures;
   analyzing the model of the one or more anatomical structures to determine a statistical correlation between the model of the one or more anatomical structures and data for an aggregation of model of the one or more anatomical structures for other breasts, wherein the analysis of the model of the one or more anatomical structures to determine the statistical correlation comprises:
extracting at least one feature associated with a type of the anatomical structure;
determining whether the extracted at least one feature indicates a likelihood of an abnormality; and
based on the determined statistical correlation, generating a risk assessment for the breast.

2. The method of claim 1, further comprising:
scanning the breast with the ultrasound probe to generate the ultrasound data;
tracking the location of the ultrasound probe during scanning of the breast; and
providing visual feedback regarding progress of the scanning.

3. The method of claim 1, wherein the risk assessment indicates whether additional diagnostic procedures should be performed for the breast.

4. The method of claim 1, the method further comprising training the artificial intelligence image analysis technique using a dataset of image data wherein structures have been previously identified.

5. The method of claim 1, wherein the one or more anatomical structures are breast ducts.

6. The method of claim 5, further comprising:
extracting from the generated model, quantitative values at least one of the number of ducts, a regularity pattern for the ducts, or a termination regularity for the ducts; and
wherein the statistical correlation is based on the extracted quantitative values.

7. The method of claim 1, wherein the one or more anatomical structures are at least one of breast ducts, lobules, lymph nodes, vascular structures, or Cooper's ligaments.

8. The method of claim 1, wherein the ultrasound data is 3D ultrasound data for the whole breast.

9. The method of claim 1, further comprising:
executing a second artificial intelligence image analysis technique to identify one or more second anatomical structures of the breast within the ultrasound image data, wherein the second anatomical structures are of a different type than the one or more anatomical structures;
removing tissue other than the identified one or more second anatomical structures from the ultrasound image data;
generating, from the identified one or more second anatomical structures, a second model of the one or more second structures of the breast, wherein the second model comprises one of:
a 3D mapping of the anatomical second structures; and
a plurality 2D mapping of the anatomical second structures.

10. A system for imaging ducts of a breast, the system comprising:
at least one processor; and
memory, operatively connected to the at least one processor, storing instructions that when executed by the at least one processor cause the system to perform a set of operations comprising:
receiving ultrasound image data for a breast scanned with an ultrasound probe;
executing an artificial intelligence image analysis technique to identify one or more anatomical structures of the breast within the ultrasound image data;
removing tissue other than the identified one or more anatomical structures from the ultrasound image data;
generating, from the identified one or more anatomical structures, a model of the one or more structures of the breast, wherein the model comprises one of:
a 3D mapping of the anatomical structures; and
a plurality 2D mapping of the anatomical structures;
comparing the extracted at least one feature to a threshold value, wherein the threshold value is determined based on data for an aggregation of models of the one or more anatomical structures for other breasts; and
based on the comparison of the extracted at least one feature to the threshold value, generating a risk assessment for the breast.

11. The system of claim 10, wherein the one or more anatomical structures are at least one of breast ducts, lobules, lymph nodes, vascular structures, or Cooper's ligaments.

12. The system of claim 10, wherein the extracted at least one feature is represented by a quantitative value.

* * * * *